US009216297B2

(12) United States Patent
Kast et al.

(10) Patent No.: US 9,216,297 B2
(45) Date of Patent: Dec. 22, 2015

(54) FLEXIBLE RECHARGE COIL TECHNIQUES

(75) Inventors: John E. Kast, Hugo, MN (US); Randy S. Roles, Elk River, MN (US); Bruce D. Fishbeck, Minneapolis, MN (US); Thipphaphone Lougiu, Brooklyn Park, MN (US); Todd A. Kallmyer, Tempe, AZ (US); Jay T. Eisch, Wyoming, MN (US); David P. Olson, Minnetrista, MN (US); William C. Phillips, Brooklyn Park, MN (US); Matthew C. Lukasek, Green Isle, MN (US); Lonnie B. Gades, Eden Prairie, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 896 days.

(21) Appl. No.: 13/053,775

(22) Filed: Mar. 22, 2011

(65) Prior Publication Data

US 2011/0245892 A1    Oct. 6, 2011

Related U.S. Application Data

(60) Provisional application No. 61/320,926, filed on Apr. 5, 2010.

(51) Int. Cl.
*A61N 1/378* (2006.01)
*A61N 1/372* (2006.01)

(52) U.S. Cl.
CPC ............ *A61N 1/3787* (2013.01); *A61N 1/37229* (2013.01); *Y10T 29/49016* (2015.01)

(58) Field of Classification Search
USPC ............................................... 607/33, 34, 61
See application file for complete search history.

(56) References Cited

U.S. PATENT DOCUMENTS

| 6,647,296 | B2 | 11/2003 | Fischell et al. |
| 7,672,732 | B2 | 3/2010 | Sun et al. |
| 2002/0087204 | A1 | 7/2002 | Kung et al. |
| 2004/0176818 | A1 | 9/2004 | Wahlstrand et al. |
| 2009/0118796 | A1 | 5/2009 | Chen et al. |
| 2009/0276016 | A1* | 11/2009 | Phillips et al. .................. 607/61 |

FOREIGN PATENT DOCUMENTS

| WO | WO2008109058 A1 | 9/2008 |
| WO | 2009029977 A1 | 3/2009 |
| WO | 2009134466 A1 | 11/2009 |

OTHER PUBLICATIONS

PCT International Search Report and Written Opinion dated Jun. 8, 2011.

* cited by examiner

*Primary Examiner* — Joseph Dietrich
(74) *Attorney, Agent, or Firm* — Beth L. McMahon

(57) ABSTRACT

Techniques adapted for use with recharging a rechargeable power source of an implantable device. One aspect relates to providing a flexible primary coil that can be transcutaneously coupled to a secondary coil of the implantable device. Multiple adjacent turns of the coil are grouped via lacing to form bundles. The bundles have at least one dimension that is selected to be a same size as a predetermined thickness of the coil. In one embodiment, the dimension is a diameter of the bundle. In another embodiment, the dimension is at least one of a length or width of the bundle. Insulating overmolding may be provided over the coil. In one embodiment, the resulting antenna structure is bidirectional such that substantially the same performance characteristics are obtained during recharge regardless of which of two major surfaces of the antenna is placed in proximity to the patient.

36 Claims, 18 Drawing Sheets

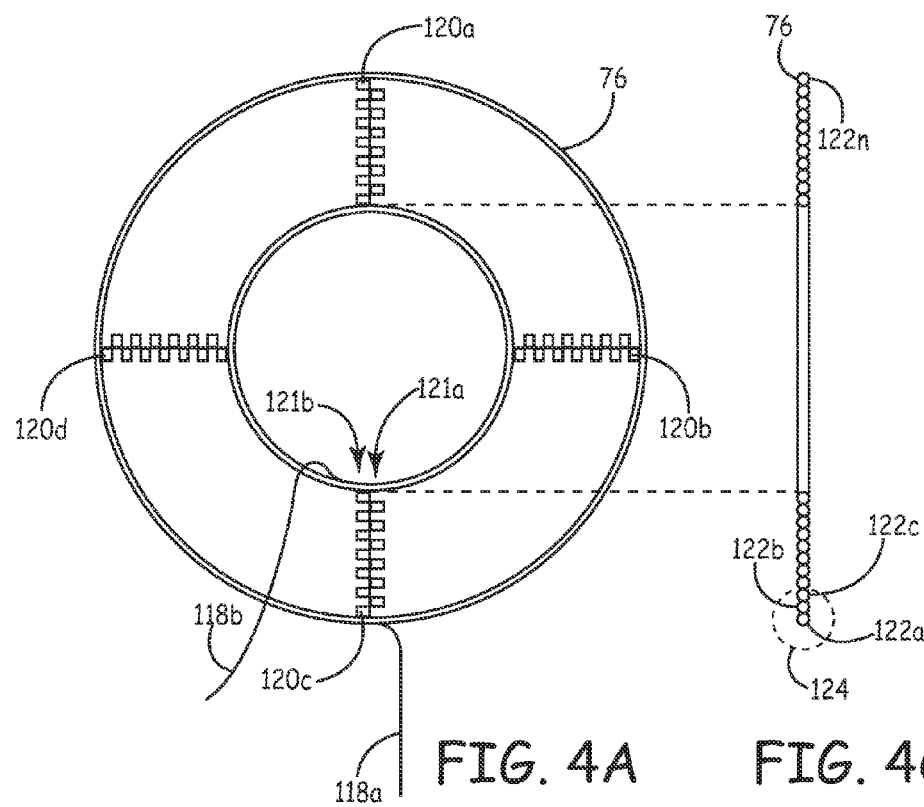
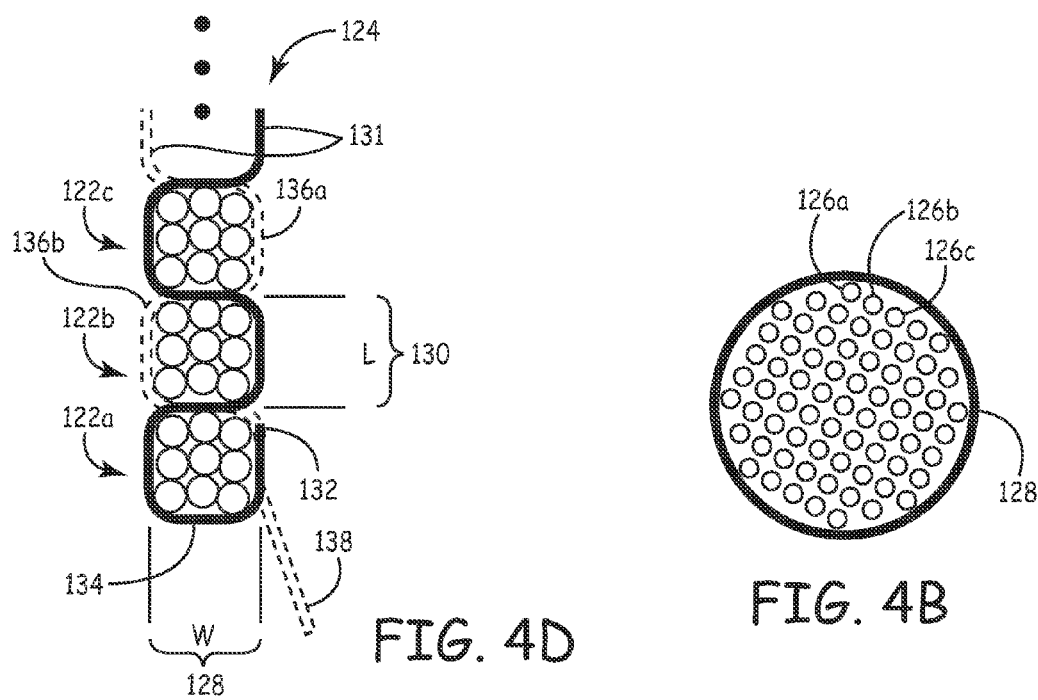
FIG. 4A FIG. 4C FIG. 4D FIG. 4B

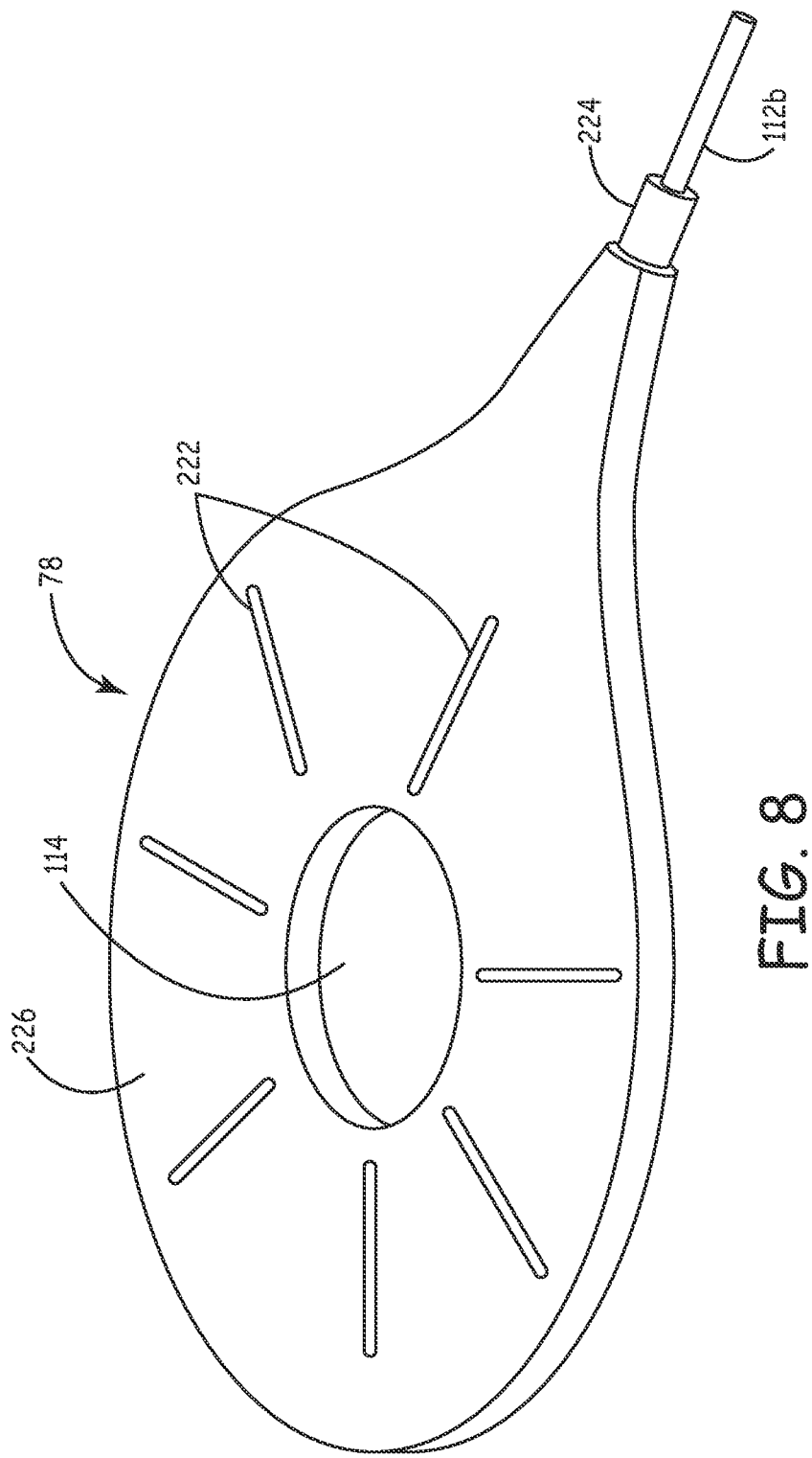

FLEXIBLE RECHARGE COIL TECHNIQUES

RELATED APPLICATIONS

This application claims priority to provisionally-filed U.S. Patent Application 61/320,926 filed Apr. 5, 2010, which is incorporated herein by reference in its entirety.

BACKGROUND

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators and cochlear implants. Of course, it is recognized that other implantable medical devices are envisioned which utilize energy delivered or transferred from an external device.

A common element in all of these implantable medical devices is the need for electrical power in the implanted medical device. The implanted medical device requires electrical power to perform its therapeutic function, which may include driving an electrical infusion pump, providing an electrical neurostimulation pulse or providing an electrical cardiac stimulation pulse. This electrical power is derived from a power source.

Some implantable medical devices can receive electrical power transcutaneously through the use of inductive coupling. For instance, power can be transferred by inductively coupling an external primary coil that is positioned on or near the skin of a patient with a secondary coil that is coupled to, or included within, an implantable medical device. Current induced in the secondary coil may be used to store energy in a power source such as a rechargeable battery and/or could be used to directly power circuitry within the implantable device. Once recharged, the internal power source may be used to supply electrical power to the implanted medical device.

Many devices and techniques have been developed to provide transcutaneous energy to power an implantable medical device and/or to recharge a power source associated with the device. As previously noted, techniques generally employ a primary coil driven by an external power source.

SUMMARY

Techniques are disclosed for transcutaneously transferring energy to an implantable medical device. A primary coil is provided that is formed of multiple turns of a conductor. Unlike in prior art designs, adjacent turns of the coil are not affixed to one another to form a rigid solid structure. Rather, one or more sets of lacing are used to form bundles of adjacent coil turns. In one embodiment, the bundles are sized so that a length and width of each bundle is substantially the same size as the desired thickness of the coil. The resulting structure is flexible so that it conforms to curves in the patient's body. At the same time, the structure maintains its shape so that superior coupling properties are maintained that will allow recharge operations to complete as quickly as possible. In one specific embodiment, the lacing is formed of a flexible tape having a pressure-sensitive adhesive backing, such as Kapton® tape.

In one embodiment, the coil is carried within an antenna structure that is formed of a thermoplastic material that allows heat generated during the recharge process to be readily and evenly distributed throughout the antenna structure to enhance patient comfort and reduce the temperature to which the patient's skin is exposed.

According to another aspect, the antenna structure may have two major surfaces, a top surface and a bottom surface. Each of these surfaces may be equidistance from a corresponding surface of the coil. That is, a top surface of the coil is substantially the same distance from a top surface of the antenna as a bottom surface of the coil is from the bottom surface of the antenna. This results in a bi-directional antenna structure, exhibiting substantially the same recharge capabilities and inductive coupling properties regardless of which of the two major antenna surfaces is located closest to (e.g., is placed again the skin of) the patient. Because of this, the patient need not be concerned with which of the two faces of the antenna is positioned closest to their body prior to initiating a recharge session. One or both major surfaces of the antenna may carry protrusions that are adapted to aid in heat dissipation, further increasing patient comfort.

The antenna may include at least one temperature sensor such as a thermistor that is located to provide an indication of the amount of heat to which the patient is being exposed during recharge. In one embodiment, two temperature sensors may be carried by the antenna, each to provide a useful measurement of heat to which the patient is being exposed during recharge when a respective face of the antenna is located closest to the patient's body. For instance, each temperature sensor may be carried at a predetermined location relative to a corresponding face of the antenna.

Another aspect of the system provides a circuit assembly that is carried by a cable that is coupled to the coil. The circuit assembly may include the components that will drive the coil with a selected signal during recharging. The components may also provide communication capabilities that can transfer data to, and/or receive data from, an implantable device via a communication session conducted via the recharge coil. In one example embodiment, short-range inductive telemetry capabilities may be provided. In another embodiment, long-range telemetry capabilities may be provided. By locating the circuit assembly within a cable that is coupled to the antenna rather than in the antenna itself, the antenna profile is minimized while coil flexibility is maximized.

Moreover, because the antenna drive circuit is located on the cable rather than in separate external device to which the antenna may be coupled, there is no need to provide any special-purpose external device (e.g., a specialized recharger or programmer) that is adapted for a particular antenna configuration, IMD configuration, or implant scenario. That is, any "special purpose" logic that generates the recharge signal in a manner that is based on characteristics of the primary coil and/or a specific IMD type is carried in this circuit assembly that "travels" with the recharge coil such that there is no requirement that a special-purpose external device be provided for this purpose.

The antenna may further carry a tuning capacitor that is electrically-coupled in series with the coil. The capacitance of this element is selected so that the resonant frequency of the system is substantially a predetermined desired frequency. A high-voltage node between the capacitor and the coil is insulated and protected by overmolding material used to form the antenna. If the capacitor were otherwise located with components of the circuit assembly carried by the cable, the high-voltage node would be located in the cable. This could undesirably pose a risk of patient shock should damage occur to the cable.

Another aspect relates to a method of manufacturing the antenna assembly. In one embodiment, this is accomplished using an injection molding process that involves multiple shots of material. For instance, a first shot of material may be applied to encase the coil within a structure that is configured to retain the coil substantially within a middle of a second-shot mold during a second stage of the molding process. After the second shot of material is applied, the resulting antenna structure includes a coil that is equidistant from either of the two major surfaces, or faces, of the antenna in the manner described above. That is, the antenna structure is bidirectional.

According to one embodiment, a charging system is provided that is adapted to charge a power source of an implantable medical device. The charging system includes a coil having multiple turns and being adapted to transcutaneously transfer an electromagnetic waveform to the implantable medical device. The system further includes lacing that is adapted to group the turns into multiple bundles, each containing a predetermined number of adjacent ones of the turns. A flexible overmolding may be formed over the coil, which in one embodiment is formed of a thermoplastic elastomer. The overmolding may form a structure having two major surfaces, and the coil may be substantially centered between the surfaces.

The lacing may, in one instance, comprise a flexible tape having adhesive adapted to adhere to the turns of the coil. The lacing may be woven between adjacent ones of the bundles. If desired, multiple sets of lacing may be provided, with each set being woven between adjacent ones of the bundles. In a particular embodiment, at least four sets of lacing may be provided. The bundles may be formed so that each bundle has a length and width that is of substantially a same dimension as a desired thickness of the coil. In one case, the predetermined thickness of the coil is no greater than 0.165 inches and the coil has a stiffness of substantially five pounds per inch.

The system may further include an external device to exchange data with the implantable medical device. A cable may detachably couple the coil to the external device. A cable may be adapted to couple the coil to a source of power. A circuit carried by the cable may be adapted to generate a signal within the coil. The circuit may be adapted to generate a signal that provides data or power transcutaneously to the implantable medical device. At least one temperature sensor may provide an indication of temperature associated with operation of the coil. A tuning capacitor may be positioned in proximity to the coil to select a resonant frequency of the system.

Another embodiment relates to a system to transcutaneously recharge a power source of an implantable medical device. The system comprises a primary coil having multiple turns, and lacing adapted to group adjacent ones of the turns into bundles, each bundle having a dimension that is substantially the same as a desired dimension of the primary coil. In one scenario, each bundle has a diameter that is substantially the same as a desired thickness of the primary coil. In a different embodiment, each bundle has a length and a width that are each substantially the same as a desired thickness of the primary coil. The lacing may be formed of multiple sets of lacing that are substantially equally spaced around a circumference of the primary coil.

The system may further include a circuit assembly to drive the primary coil with at least one of a recharge signal and a communication signal. A cable may be coupled to the primary coil that carries the circuit assembly. An overmolding may be applied to at least one surface of the primary coil to form an antenna having first and second major surfaces. The resulting structure is bidirectional. That is, the structure allows coupling efficiency between the primary coil and a secondary coil of the implantable medical device to be substantially the same regardless of which of the first and second major surfaces of the antenna is positioned closest to the secondary coil when the secondary coil is receiving energy from the primary coil.

The system may further comprise first and second temperature sensors, each to provide a temperature associated with a respective one of the first and second major surfaces of the antenna when the secondary coil is receiving energy from the primary coil.

Yet another aspect relates to a holster having a pocket with a first side and a second side. The holster is adapted to carry the primary coil during recharging operations. The pocket is adapted to receive the primary coil from either the first side or the second side. The primary coil may be rotated by at least 90 degrees within the pocket when received from either the right side or the left side of the pocket.

A method of making an antenna is also disclosed. The method includes winding a conductor to form a coil having multiple turns and first and second surfaces. Adjacent turns of the coil are grouped into bundles, each having a dimension that is substantially the same as a predetermined thickness of the coil. For instance, each bundle may have a length or a diameter that is the same as the predetermined thickness of the coil. The grouping of the multiple turns into bundles may be performed either after all turns of the coil are wound or as the turns are being wound. In the latter case, a bundle may be formed after a predetermined number of coil turns to be included in the bundle are wound.

A flexible insulation may be provided over the coil. In one embodiment, the flexible insulation is applied by providing a first shot of material to form retaining members over the coil. The retaining members are positioned within a second shot mold and a second shot of material is applied such that a first major face of the antenna is substantially a same distance from the first surface of the coil as a second major face of the antenna is from a second surface of the coil. Another aspect may include providing a cable carrying a circuit assembly, and coupling the cable to the coil to allow a circuit of the circuit assembly to drive the coil.

In one case, the step of winding the conductor may include winding the conductor around a rod having at least one flange, and removing a portion of the flange to group the adjacent turns of the coil.

Other aspects of the disclosure will become apparent from the following description and the accompanying drawings.

BRIEF DESCRIPTION OF THE DRAWINGS

FIG. 4A is a top view of a coil according to one embodiment.

FIG. 4B is a cross-sectional view of one embodiment of a conductor used to form a coil of one embodiment.

FIG. 4C is a side cross-sectional view of a coil showing adjacent turns of the conductor being grouped into multiple bundles.

FIG. 4D is an exploded view of the highlighted area of FIG. 4C.

FIG. 8 is a perspective view of an antenna following application of a second shot of material.

DETAILED DESCRIPTION

Techniques are disclosed for providing a recharging system having a primary coil that is flexible, retains its thin pliable shape during the overmolding process, and is durable and fault-resistant over many cycles of use.

Figure 1:
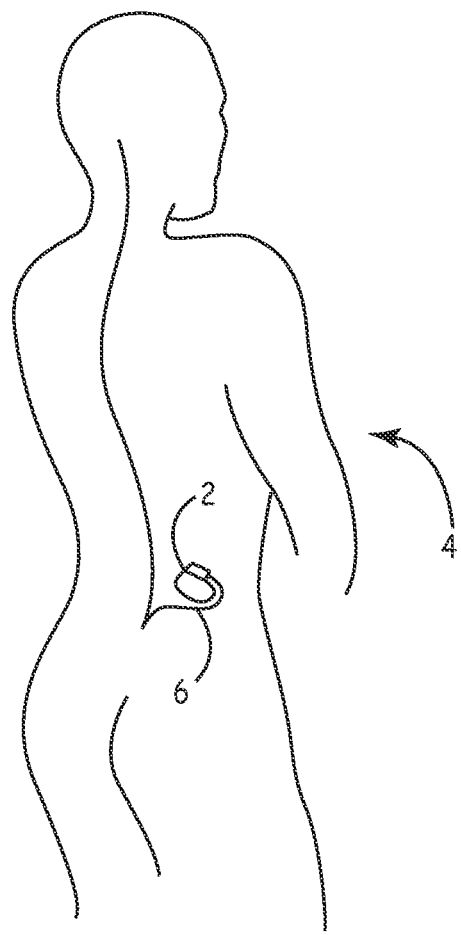
FIG. 1 is a diagram illustrating an exemplary Implantable Medical Device, which may be a neurostimulator, implanted in patient.

FIG. 1 shows an exemplary IMD 2 that may take advantage of a charging system such as disclosed herein. IMD may be adapted to deliver a type of therapy to the patient, which may include electrical stimulation and/or drug therapy. Many types of implantable medical devices may utilize the disclosed recharging systems and techniques, including implantable therapeutic substance delivery devices, implantable drug pumps, cardiac pacemakers, cardioverters or defibrillators, and/or devices to deliver electrical stimulation pulses for a neurological or muscular condition. Other specific examples include devices to provide therapy to treat chronic pain, tremor, Parkinson's disease, epilepsy, urinary or fecal incontinence, sexual dysfunction, obesity, or gastroparesis. Such therapy may be delivered via one or more therapy connections 6, which may be one or more leads and/or catheters. The patient's body may carry additional IMDs which may be similar to, or different from, IMD 2.

Figure 2:
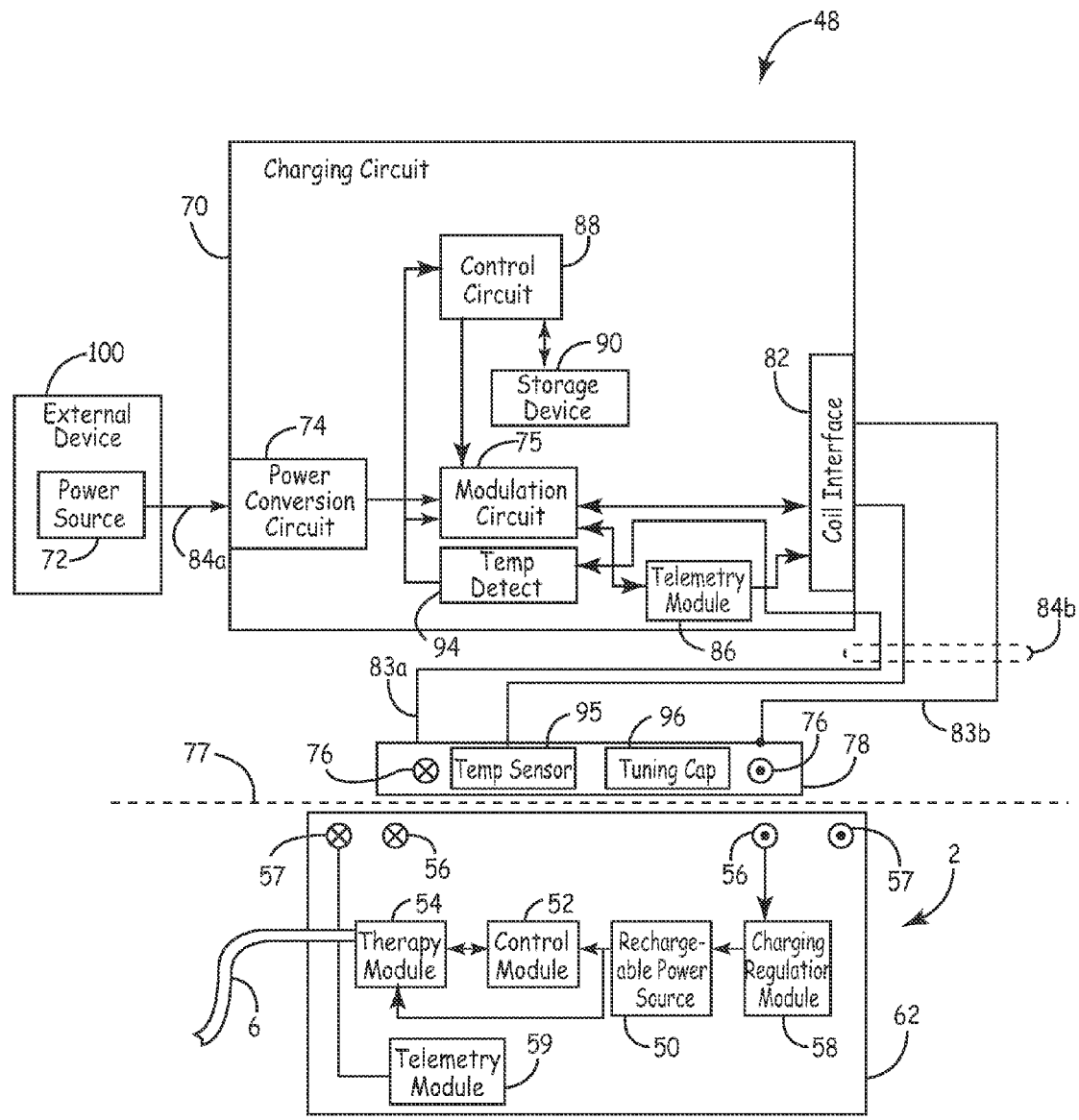
FIG. 2 is a block diagram of one embodiment of the Implantable Medical Device of FIG. 1 and a charging device for recharging a power source of the IMD.

FIG. 2 is a block diagram of an exemplary charging system 48 that may usefully employ one or more of the techniques disclosed herein to recharge IMD 2. IMD 2 includes a rechargeable power source 50. Rechargeable power source 50 may be chemically-based (e.g., a battery) or may be a device to store charge (e.g., a capacitor). In one embodiment, rechargeable power source 50 is a lithium ion battery. Any other type of rechargeable power source suitable for powering an IMD may be used in conjunction with the mechanisms of the current disclosure.

Rechargeable power source 50 may be coupled to a control module 52, which includes circuitry to control therapy delivered to the patient. Control module 52 may include one or more microprocessors, application-specific integrated circuits (ASICs), digital signal processors (DSPs), field-programmable gate arrays (FPGAs), discrete electronic components, state machines, sensors, and/or other circuitry.

Control module 52 may further be coupled to therapy module 54, which delivers some form of therapy to a patient. This therapy may include controlled delivery of a substance and/or electrical stimulation. For example, in one embodiment, therapy module 54 may include one or more output pulse generators such as capacitive elements, voltage regulators, current regulators, voltage sources, current sources, and/or switches that are coupled to rechargeable power source 50 directly or through control module 52. Therapy module 54 may deliver electrical pulses to patient 4 via a combination of electrodes. As shown in FIG. 1, therapy module 54 may be coupled to patient 4 through one or more therapy connections 6 such as leads and/or catheters. Alternatively or additionally, the can of IMD 2 may carry or otherwise provide one or more electrodes for delivering therapy. As yet another possibility, IMD 2 may wirelessly communicate with and/or control one or more other implantable devices (e.g., microdevices) within the patient's body that likewise provide therapy and/or obtain sensed signals.

In one embodiment, rechargeable power source 50 may be coupled to a secondary coil 56 (shown in cross-section) through a charging regulation module 58. During a recharge session, a current is induced in secondary coil 56 which is provided to charging regulation module 58, which controls the charging of rechargeable power source 50.

IMD 2 may also include a telemetry module 59 coupled to a dedicated telemetry coil 57 (shown in cross-section) or telemetry may be performed using secondary coil 56 for both recharge and telemetry. Telemetry module 59 may utilize various types of telemetry protocols to communicate with external recharging device 70. A proximity telemetry system is utilized for telemetry distances of 5 centimeters or less. An arm's length telemetry system is employed for distances of up to 1 meter. This latter type of system may utilize the electric field (E-field) component of a propagating wave to transmit information (e.g., the MICS band set aside for medical device telemetry.) Arm's length telemetry may also be achieved using the magnetic (H-field) component or coupled-coil transmission. Distance telemetry systems using E-field communication may be employed when separations between the antenna and the target device exceed arm-length.

Rechargeable power source 50, charging regulation module 58, control module 52, therapy module 54, telemetry module 59, secondary coil 56 and telemetry coil 57 may be contained in a hermetically sealed housing 62. Alternatively, secondary coil 56 may be attached to, or positioned on, an exterior surface of sealed housing 62, or may be umbilically-coupled to the IMD via a cable. In one embodiment, a magnetic shield 66 may be positioned between secondary coil 56 and other electronics to substantially increase the amount of energy captured by the secondary coil and protect the electronics from electromagnetic energy when secondary coil 56 is utilized to charge rechargeable power source 50.

As previously discussed, FIG. 2 further illustrates a charging system 48 for recharging rechargeable power source 50 of IMD 2. Charging system 48 includes a charging circuit 70.

This circuit receives power from a power source 72, which may be a wall outlet, prime cell, or rechargeable battery. Power source 72 may be provided by a recharge cradle that includes batteries or is coupled to a wall outlet. Power received from the power source is provided to power conversion circuit 74, which supplies appropriate power levels to modulation circuit 75.

Modulation circuit 75 is a signal generator to generate a recharge signal of a desired frequency, typically somewhere between 8 KHz and 500 KHz. In one embodiment, modulation circuit 75 comprises an H-bridge circuit. The recharge signal may be a sine wave or some other type of signal, if desired. The frequency of the recharge signal may depend on the resonant frequency of the system, which takes into account the loading placed on the system when secondary coil 56 is inductively coupled across cutaneous boundary 77 (shown dashed) to primary coil 76. Charging circuit 70 may vary the frequency during a charging session to find the resonant frequency of the system which will result in optimal charging efficiency. In one specific embodiment described herein, the resonant frequency is substantially around 41 KHz.

The signal generated by modulation circuit 75 is provided to drive primary coil 76 via coil interface 82 and signal lines 83a and 83b. Primary coil 76 may be of many different configurations. The size, shape, and number of turns of the coil will generally be selected based on the size and shape of secondary coil 56, as well as the implant scenario associated with IMD 2. For instance, if IMD 2 is intended for use in a deep implant scenario, it may be desirable to configure primary coil 76 to include a large number of coil turns, since this will result in the generation of a larger magnetic field, which will be needed to achieve adequate inductive coupling at the greater implant depth. A larger number of turns may likewise be needed if primary coil 76 is intended for placement at some distance from cutaneous boundary 77 instead of being placed directly on this boundary, as may be applicable for some implant scenarios. For instance, this may be the case when an insulator or a cooling device is positioned between the primary coil 76 and the cutaneous boundary.

Coil may be housed within an antenna 78, which may be a structure made of a material that is an electrical insulator. For instance, it may be made of a polymer that has a comfortable texture suitable for placement against the skin of the patient. In one embodiment, antenna 78 is made of a thermally-conductive elastomer material that is capable of spreading heat generated by coil 76 over a wider surface to increase patient comfort during recharge.

Charging circuit 70 may have a telemetry module 86 enabling communication with IMD 2 during a charging session to provide status or other information concerning the charging session. Telemetry module 86 may be adapted to utilize various types of telemetry protocols, including a proximity protocol for telemetry distances of 5 centimeters or less or an arm's-length telemetry protocol for distances of up to, or even exceeding, 1 meter. In one specific embodiment, telemetry module 86 is adapted to utilize a proximity protocol to communicate with IMD 2 via primary coil 76. Secondary recharge coil 56 may be used to transmit/receive such a communication to/from primary coil 76. Alternatively, a dedicated telemetry coil such as telemetry coil 57 may be provided within IMD 2 for this purpose, as previously described.

In one embodiment, recharging device 70 may be automatically activated using a telemetry signal received from IMD 2. For instance, recharging device 70 may continuously send out requests via telemetry communication. When IMD 70 is in proximity to rechargeable power source 50, IMD 2 sends an acknowledgement so that recharging device 70 may initiate a recharge session.

Charging circuit 70 may be controlled by control circuit 88, which may include one or more microprocessors, FPGAs, ASICs, DSPs, microsequencers, discrete components, and/or other electronic circuit components. Control circuit 88 may provide control signals to indicate how modulation circuit 75 is to drive primary coil 76, for instance. In an embodiment wherein control circuit 88 operates according to programmed instructions, control circuit 88 may be coupled to one or more storage devices 90, or may otherwise include such storage devices. Storage device(s) 90 may include volatile, non-volatile, magnetic, optical, and/or electrical media for storing digital data and programmed instructions, including random access memory (RAM), read-only memory (ROM), non-volatile RAM (NVRAM), electrically erasable programmable ROM (EEPROM), flash memory, removable storage devices, and the like.

In one embodiment, charging circuit 70 may include a temperature detection circuit 94. This circuit receives one or more signals from at least one temperature sensor 95 that is carried by antenna 78 and is in proximity to coil 76. Temperature sensor 95 provides one or more signals to temperature detection circuit 94 to allow the charging circuit 70 to determine whether temperature limits are being met during recharge. Such limits may be based on government regulations, patient preferences, and/or some other standard, and in some cases may be user-selectable (e.g., programmably selectable by a clinician or patient). If a detected temperature is exceeding a predetermined limit, temperature detection circuit 94 will provide a signal to control circuit 88. This may cause control circuit 88 to alter the signal driving the antenna 78 so that the temperature of the antenna will be reduced to within acceptable limits.

As discussed above, charging circuit 70 receives energy from a power source 72, which in one embodiment, may be selectable by the user to be any one of an AC wall outlet, rechargeable batteries (e.g., lithium ion batteries) or prime cell batteries. In one scenario, the external device 100 may be a patient or clinician programmer used to exchange data (e.g., programming commands, patient information, status information, etc.) with IMD 2.

External device 100 may couple to charging circuit 70 over interface 84a. This interface may be a cable that removably plugs into a connector of the external device. Such a configuration allows charging circuit 70 and coil 76 to be removably coupled to the external device 100. The connector provided for this purpose may be designed according to an industry-standard (e.g., Universal Serial Bus standard) or may be a proprietary-type connector.

Turning now to additional aspects of antenna 78, primary coil 76 is adapted to transfer an electromagnetic waveform to secondary coil 56. The electromagnetic waveform may comprise a communication signal and/or a signal to transfer power to the IMD. For instance, communication may occur during a distinct periodic "telemetry" phase of operation. Primary coil 76 may be selected to be of a similar size and shape as secondary coil 56.

This will generally result in better inductive coupling between coils and will typically provide better energy transfer to the rechargeable power source 50. The number of turns of the primary coil 76 may be selected based on the likely implant depth and orientation of the IMD within a patient. For instance, if IMD 2 will likely be employed in an implant scenario involving a deep or angled implant, or if the coils are to be retained at some distance from cutaneous boundary 77 during recharge, it may be desirable to utilize a primary coil having an increased number of turns, which, in turn, will increase the magnetic field produced by this coil when the coil is driven with a given input signal. This increases magnetic field strength, as may be necessary to achieve adequate inductive coupling between the primary coil 76 and the secondary coil 56 in these types of situations.

The configuration selected for primary coil 76 (e.g., size, shape, number of turns) will determine the inductance of the primary coil. This inductance, along with the capacitance and resistance of the system will, in turn, affect the resonant frequency at which the system is most efficiently driven. To tune the system so that this resonant frequency is at, or near, some predetermined desired resonant frequency, a tuning capacitor 96 having a selected capacitance is electrically coupled in series with coil 76. Thus, returning to FIG. 2, coil 76 and tuning capacitor are coupled in series between signals 83a and 83b, which are driven by modulation circuit 75.

In one embodiment, tuning capacitor 96 is carried within antenna 78 in proximity to coil 76. A tuning capacitor having a capacitance of 12 nF is selected in one embodiment, resulting in a resonant frequency of substantially 41 KHz. Of course, many other frequencies may be selected as the resonant frequency with the value of the capacitor being selected accordingly as is known in the art.

When coil 76 is being driven with an oscillating signal, as will occur during recharge, the node electrically coupling capacitor 96 to coil 76 will "ring up" to a high amplitude that could approach several hundred volts. Positioning the tuning capacitor 96 within antenna will ensure that this high-voltage node is well insulated by the electrically-insulating material used to form antenna. An alternative embodiment may locate tuning capacitor 96 within circuit 70 that is situated remotely from antenna 78. This would place the high-voltage node within interface 84b (shown dashed), which may not be desirable if a cable that embodies this interface is damaged. Such a scenario may pose a shock risk. Thus one embodiment places tuning capacitor 96 within antenna 78 to avoid this risk of shock.

Figure 3:
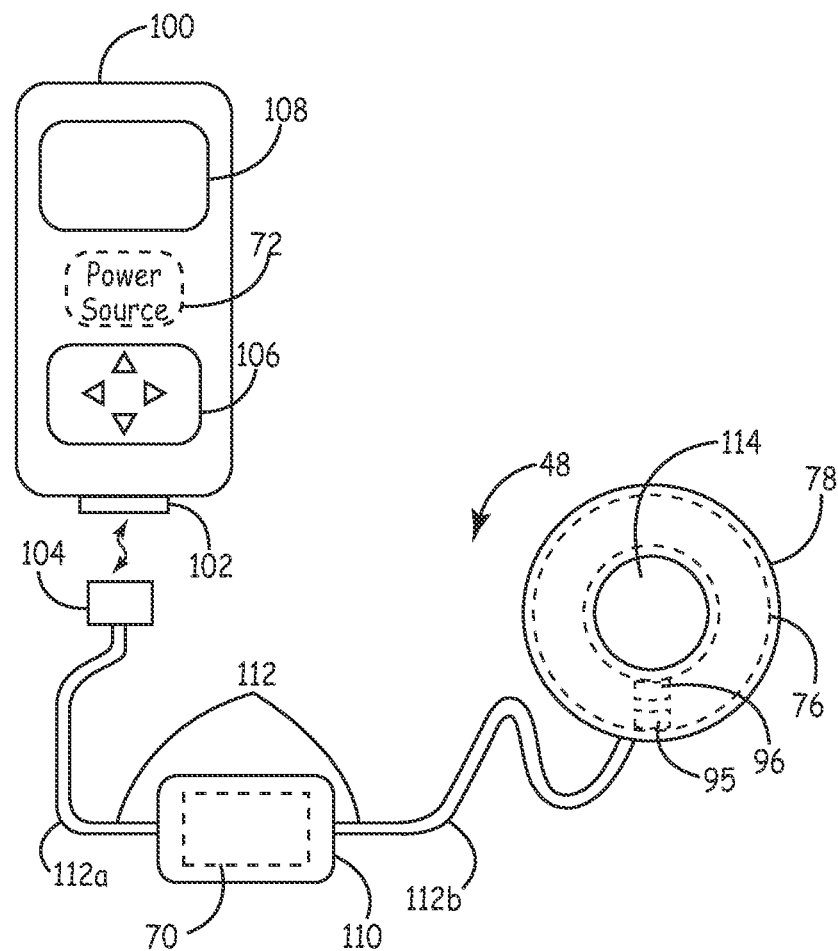
FIG. 3 is a system representation the charging system of FIG. 2

FIG. 3 is a system representation of the charging system 48 of FIG. 2 coupled to an external device 100 that is shown to be a hand-held patient programmer. In another embodiment, external device 100 could be a clinician programmer that may be a portable device, a laptop or tablet computer, a desktop data processing system, or another type of data processing system. As one example, external device could be a device adapted to interface, either wirelessly or via wired connections, to one or more other devices. Such types of programmers may be employed by a user to perform programming and monitoring tasks associated with IMD 2, as is known in the art. For instance, the programmer may be used to initially configure the IMD after implant, to modify therapy that is being delivered to the patient 4, to obtain data from the IMD indicative of patient, therapy and/or system status, and so on.

In another example, external device 100 need not have programming capabilities, but could be a device solely dedicated to initiating, controlling, and/or presenting status associated with recharging rechargeable power source 50.

External device 100 may have a user interface that may include a key pad 106, a display screen 108, and one or more other input/output mechanisms. Such mechanisms may include dedicated buttons, gesture-based control capabilities (e.g., scroll wheels or swipe functionality, etc.), voice-detection or sound-emitting capabilities, and so on. Display screen 108, which may be a LED, LCD, LED-LCD, OLED, or any other type of screen known in the art, may provide color and touch-screen functionality.

As discussed above, external device 100 may be powered by power source 72 (shown dashed), which may be a prime cell battery, a rechargeable battery and/or a circuit designed to couple to a wall outlet. This power source may provide charging circuit 70 (shown dashed) with the power and ground signal levels needed for circuit operation.

In one embodiment, charging circuit 70 may be removably coupled to external device 100. In particular, charging circuit 70 may be electrically coupled to a cable 112 that is equipped with a connector 104 that plugs into connector 102 of external device 100. Connectors 102 and 104 may be of many types. In one embodiment, the connectors comply with electrical and/or mechanical aspects set forth in an industry standard specification, such as the electrical characteristics outlined by the Universal Serial Bus (USB) Specification. Alternatively or additionally, the connectors may have one or more aspects that conform to a proprietary format.

In some embodiments, connector 104 of cable 112 may be adapted to interface with multiple types of external devices that provide standard voltage and ground connections utilized by connector 104. For instance, if connector 104 has standard voltage and ground connections specified by the USB specification, any type of external device that is adapted to mechanically receive connector 104, that provides these standard voltage and ground connections, and that is capable of satisfying the power requirements of charging circuit 70 may be used to power recharger. For instance, a personal PC such as a laptop or other tablet device could be used for this purpose.

According to one example, external device 100 may be adapted to detect when it has been coupled to charging system 48 and respond accordingly. For instance, this may involve automatically presenting a user interface display via screen 108 that provides the capabilities to allow a user to initiate a recharge operation, as may be accomplished by selecting appropriate key strokes of keypad 106, engaging a touch screen interface, or using some other user interface mechanism. Thus, by merely plugging charging system 100 into connector 102, external device 100 automatically becomes configured for use in performing the recharge operation without any additional interaction on the part of the user such as the need to navigate to an appropriate recharge screen to initiate this operation.

Charging circuit 70 may be housed within a circuit module 110 that is carried by cable 112. Specifically, a portion 112a of cable 112 may provide interface 84a (FIG. 2) coupling external device 100 to charging circuit 70. A second portion 112b of cable 112 may provide interface 84b (FIG. 2) coupling charging circuit to antenna 78.

Circuit module 110 may be of many different shapes and sizes. In one embodiment, it may be a tubular component that is wider than the rest of cable 112. In one instance, all of the components shown in FIG. 2 to be included within charging circuit 70 may reside within circuit module 110. In other embodiments, any one or more of the components shown to be included within charging circuit 70 may instead reside within external device 100. In yet additional embodiments, components in addition to those shown in FIG. 2 may be housed within circuit module 110. For instance, circuit module 110 may provide some user interface capabilities, such as one or more buttons that may be employed by a user to initiate recharge, a display screen or other visual indicators (e.g., LEDs, etc), or any of the other user interface capabilities described herein. In alternative embodiments, one or more of the circuit components shown in FIG. 2 to be included within charging circuit 70 may be located within antenna 78.

Allowing one or more of the circuit components of charging circuit 70 to be carried by circuit module 110 rather than external device 100 has advantages. For instance, the circuitry needed to drive antenna 78 will generally be tailored to drive a specific antenna configuration, as discussed above. For instance, modulation circuit 75 and/or control circuit 88 may be configured to drive an antenna having a particular resonant frequency and loading characteristics based on the associated tank circuit. Moreover, the antenna and drive circuit may be configured based on a type of IMD 2 and/or implant scenario with which the components will be used. As an example, the resonant drive frequency and power level at which coil 76 is driven by modulation circuit 75 and control circuit 88 may be based, in part, on such things as a known characteristic of secondary coil 56, charging regulation module 58, and/or rechargeable power source 50, a known implant depth, or other aspects of IMD 2 or a particular implant scenario.

When housed within circuit module 110, the circuitry for a particular antenna will be attached to, and "travel with", the antenna for which it is designed, rather than being incorporated into a specific external device. This eliminates the need to have different versions of an external device, each being adapted to drive a corresponding antenna configuration and/or to recharge a particular type of implantable medical device. The external device need only have the appropriate connector and expected power and ground levels to drive any number of antenna configurations that can be used with a variety of implantable medical devices. Additionally, locating circuitry within circuit module 110 rather than within antenna 78 helps to minimize the size, weight, and profile of the antenna. This may make the antenna easier for the patient to handle. Further, heat generated by charging circuit 70 may be readily dissipated when carried on the cable without contributing to heating of antenna 112 during recharge.

According to a different paradigm, charging system 48 may be modular. That is, antenna 78 may be removably-connected to cable portion 112b, which in turn may be removably connected to circuit module 110. Circuit module 110 may likewise be removably-connected to cable portion 112a. This "plug-and-play" capability allows various circuit modules to be coupled to a range of antennas so that systems may be more specifically tailored for a type of implant. For instance, the system may be tailored for a specific type of implant device by selecting size and shape of the primary coil. The system may further be tailored for an appropriate implant scenario (e.g., implant depth, angle of implant) by selecting a drive strength of the circuit module.

In the type of modular system described above, the length of cable portions 112a and 112b may, in one case, be selected based on user preferences so that circuit module 110 may be located in a desired position relative antenna 78. For instance, some users may prefer that circuit module 110 is located closer to antenna 78 so that this object is less likely to be swinging freely during recharge. Other users may want the circuit module to be located closer to connector 104, possibly allowing this module to be carried within a pocket of a jacket or otherwise carried by clothing. In one embodiment, circuit module 110 may even have clips or hooks to allow fastening this module to clothing in some fashion. In one particular embodiment, cable portion 112a is about half the length of cable portion 112b so that circuit module 110 is one-third the distance from external device 100 to antenna 78.

Cable 112 may be a shielded cable having an external insulating jacket that may be formed of nylon, urethane, silicone, rubber, or some other insulating material. In one embodiment, it is formed of Santoprene® thermoplastic rubber having a durometer of about 70 Shore.

In another example, circuit module 110 may contain a power source of its own rather than relying on receiving power from external device 100. Such a power source may include any of the types of power sources known in the art. Alternatively or additionally, circuit module 110 may be adapted to plug directly into a wall outlet or into some other source of power, such as any other device that has a power source that can provide acceptable power levels. In this latter example, charging circuit 70 may be employed to initiate and complete a recharge session without being coupled to any special-purpose external device related to recharging IMD 2.

Turning now to a discussion of antenna 78, this component may carry at least one temperature sensor 95 (shown dashed) and/or a tuning capacitor 96 (shown dashed). As previously discussed, an advantage of locating the tuning capacitor in proximity of coil 76 is that the high voltage node between the capacitor 96 and coil 76 will be well-insulated and protected by antenna 78 rather than being located within cable portion 112b (as would occur if the capacitor were included within charging circuit 70).

The configuration of antenna 78 illustrated in FIG. 3 includes a center opening 114 to allow air to flow within the center of coil 76. This cutaway portion decreases the thermal mass of this element. This may aid somewhat in heat dissipation, allow skin of a patient to "breath" during recharge, and also reduce the weight of antenna 78. Of course, many other configurations are possible, including antennas that are solid structures without such openings or cutaway portions.

FIG. 4A is a top view of coil 76. Coil 76 is formed by winding an insulated conductor multiple times around a bobbin assembly that has a central rod terminated on each end by flanges that are spaced apart a distance that corresponds substantially to the desired thickness of the coil. As the conductor is wound about the central rod of the bobbin, the flanges force the windings into a space having the desired thickness, as will be described further below.

The resulting coil can be wound to have any number of shapes, such as circular, oblong, etc. The size and shape of the coil will be determined, at least in part, by the rod around which the conductor is wound. The shape of the coil may be selected based on the IMD 2 to be recharged.

Like the shape, the number of turns within the coil may be selected based on the target implant scenario. For instance, the implant depth and location of a "typical" implanted device that will be recharged using charging system 48 may determine the number of turns, size of central opening 114, and so on. Increasing the size of the central opening and the number of turns will generally increase the strength of the magnetic coupling that will occur between coil 76 and secondary coil 56 of IMD 2. However, increasing the coil size too much may make the coil unwieldy. Thus, competing interests may be considered when determining an optimal coil configuration for a given implant scenario.

In one embodiment, a circular coil is employed having an inner diameter ranging between 1.5 and 3 inches and an outer diameter ranging between 3 and 6 inches. In one specific example, the outer diameter is about two times the size of the inner diameter (e.g., a 4 inch outer diameter and a 2 inch inner diameter.)

The coil thickness (that is, the number of turns that are "stacked" one on another) may vary based on the application. Decreasing the number of turns that are stacked one on another allows a same total number of coil turns to be spread over a larger area. This increases to overall area of the coil (e.g., by increasing the outer diameter of the coil). This, in turn, increases the area occupied by the magnetic field during recharge, making it easier for a user to locate antenna 78 at a position at which at least an adequate amount of power is being transferred to IMD 2. While coil area could be increased by simply adding more coil turns, this solution will increase the overall coil resistance, something that will result in more energy being lost as heat within antenna 78 during recharge. Such heat dissipation can lead to patient discomfort and may require power provided to primary coil 76 to be reduced, increasing time required to complete recharge. Thus, increasing area without adding turns may be preferable.

A related benefit associated with spreading coil turns over a larger area is that any heat that is dissipated by coil 76 during recharge may be dispersed more readily and over a larger area than if more turns are stacked one on another within a smaller area.

The total number of coil turns should not be decreased too much, however, since coil inductance decreases as the number of turns decreases, requiring tuning capacitor 96 to become larger to achieve a given resonant frequency. This increase in capacitor size is not desirable if the tuning capacitor 96 is to be carried by antenna 78.

In view of the foregoing, it is not desirable to allow coil 76 to become too thin (that is, allowing too few turns to be stacked one upon another). However, allowing coil thickness to increase beyond some predetermined amount is likewise not desirable. When too many turns of the coil are stacked one on another to increase the coil thickness beyond some predetermined amount, the coil may become inflexible and unable to conform to the curves of the patient's body.

In one embodiment, coil 76 has a thickness of between 0.075 and 0.3 inches. In a more specific example, the thickness may be between 0.1 and 0.165 inches. In an even more specific embodiment, the thickness is about 0.118 inches. The number of turns within the coil may range in one embodiment from 100 to 140 turns. A more specific embodiment employs a coil having between 110 and 130 turns. In a still more specific embodiment, a coil having about 120 turns may be used. The thickness of the coil will be determined by the spacing of the flanges of the bobbin around which the conductor is wound, as is discussed further below.

Generally, it is desirable to form the coil of a conductor having as high a conductivity as possible so that resistance within the coil is minimized, thereby minimizing resistive losses that result in heating during recharge. For instance, silver may be desirable since it has the highest conductivity of any metal. However, because of competing cost considerations, copper or some other conductor may be selected instead. Other less conductive materials, such as MP35N may be used for better fatigue life, with such materials being plated with a more conductive material to increase conductivity.

The coil may be comprised of Litz wire because it exhibits a lower impedance at high frequencies. Examples of Litz wire that may be suitable for this purpose include, but are not limited to, 66×42 (66 individually-insulated strands of 42 gauge wire), 25×38, 104×44, 40×42 and 110×48. In one particular embodiment, 66×42 Litz wire is selected to produce a coil having an inductance of between 1.2 and 1.3 millihenries at 41 KHz. In one specific embodiment, the coil has an inductance of substantially 1.22 millihenries at this frequency. Each strand of the Litz wire may be insulated with a single-film urethane varnish, although other materials may be used for the insulation such as silicone. The strands of the wire may optionally be twisted together to increase wire strength.

The Litz wire may further comprise an outer serving formed of nylon, vinyl, urethane, silicon, PTFE (such as Teflon PTFE). In one particular embodiment, the serving is made of Rubadue Teflon™ material available from Rubadue Wire Company. This material provides the advantage of being slippery, allowing adjacent wire turns to slide over one another without breaching the outer serving. This material also exhibits superior flex performance, allowing the wire to be flexed repeatedly without breaking. Additionally, this insulating material does not become tacky during the overmolding process, making the overmolding process easier to complete.

FIG. 4B is a cross-sectional view of one embodiment of a conductor used to form coil 76. As discussed above, Litz wire comprising multiple individually-insulated strands 126*a*, 126*b*, 126*c*, and so on, may be used for this purpose. The illustrated embodiment includes 69 such strands, however many other scenarios are possible. As previously described, the outer insulation layer 128 may be formed of Rubadue Teflon™ material, which has high flex resistance, has a non-stick surface so that adjacent strands do not "stick" together, and further exhibits superior toughness. Other materials used for this purpose may be other kinds of PTFE, silicone, nylon, other types of polyurethanes, and so on.

Returning to FIG. 4A, after the coil is wound, resulting in the example circular structure terminated by two loose ends 118*a* and 118*b* of the conductor, some mechanism is needed to retain the turns of the coil in this configuration. Prior art methods accomplish this by applying epoxy that binds adjacent windings one to another, forming a very rigid solid structure that does not conform to curves of the human body. The coil of the current disclosure improves the flexibility of the structure by bundling adjacent turns of the coil together using a lacing mechanism.

In one embodiment, one or more sets of lacing, shown as sets 120*a*-120*d*, are used to bundle adjacent turns of the coils. In particular, a predetermined number of adjacent turns of the coil are selected for inclusion in a bundle. The bundles are selected to have both a length and width that approximate the desired thickness of the coil. As previously discussed, this thickness may range between 0.1-0.165 inches. In an even more specific embodiment, the thickness is about 0.118 inches. Bundling adjacent turns in this manner produces a coil structure having a maximum degree of flexibility while still maintaining a desired shape. If bundles are made any larger, the adjacent turns tend to "bunch up", make the coil thicker while decreasing flexibility. If the bundles are made any smaller, the coil does not retain its shape and may be difficult to handle during the overmolding process. This is discussed further below.

In another embodiment, the lacing is woven so that bundles are substantially circular rather than being substantially rectangular (e.g., a square). In this embodiment, the diameter of each bundle is selected to be of a dimension that is substantially the same as the desired thickness of the coil.

FIG. 4C is a side cross-sectional view of coil 76 showing how adjacent turns of the conductor are grouped into multiple bundles 122*a*-122*n*. Three such bundles are included within highlighted area 124 (shown dashed).

FIG. 4D is an exploded view of highlighted area 124 of FIG. 4C showing bundles 122*a*-122*c*. The length 130 of each bundle is about the same as its width 128, which is also the same size as the selected coil thickness. This provides a coil have optimal characteristics, as discussed above. In one embodiment, each bundle will include a same number of turns. The current embodiment shows that each bundle includes nine adjacent turns of the coil, however more or fewer turns may be included per bundle. In a specific embodiment, a coil contains 12 bundles, each bundle containing 10 turns of the coil.

Many materials may be used to form the bundles, including films and threads such as Mylar, Kapton® polyimide, FEP Teflon® fluoropolymer, acetal copolymer, PEEK, monofilament, silk, cloth, nylon, or tapes such as, Teflon® fluoropolymer, polyimide films, nylon, PTFE and vinyl tape or other types of serving materials. As a specific example, a thin, strong, flexible adhesive tape is used. In one particular case, Kapton® high-temperature polyimide tape having a pressure-sensitive adhesive backing may be used for the lacing material. The adhesive backing allows the tape to be maintained in position on the coil as the bundles are formed. Such tape, available from 3M Corporation, withstands high temperatures and will not melt during the overmolding process that is used to form the antenna structure, as will be described below. Another type of suitable tape includes FEP Teflon® film.

Lacing of the coil may be performed during the winding process or after the winding is complete. In one embodiment wherein lacing is performed after the winding is complete, the lacing process may begin by affixing an end 132 of lacing 131 around the outer-most adjacent turns of the coil The lacing may then be wrapped around the outer edge 134 of the coil to encircle the desired number of adjacent coil turns, which in FIG. 4D is shown to be nine such turns. However any other number of turns may be selected to obtain a bundle having a length that is the same size as the width, which is also the size selected as the coil thickness. Thereafter, the tape is woven through the coil structure to the other side of the coil and the process is repeated. That is, the tape is positioned to encircle the desired number of adjacent coil turns and then again is pulled to the other side of the coil. The weaving process is continued until the tape reaches the inner edge of the coil (e.g., the edge defined by the inner circumference of the coil). The tape is wrapped to encircle the inner edge, and the weaving process continues next to the row of lacing that was just created. When the outer edge of the coil is reached, two counterpart rows of lacing will have been formed, shown as rows 121a and 121b for the lacing 120c of FIG. 4A. In FIG. 4D these two rows are depicted by a first row that is shown as a solid structure and a second row shown dashed.

The second end 138 (shown dashed in FIG. 4D) of the lacing 131 may then be wrapped around the outer-most bundle in a manner similar to that shown for end 132. Alternatively, ends 132 and 138 may be tied or otherwise affixed together.

It may be appreciated that the drawing of FIG. 4D is not to scale. In one embodiment, the tape is about 0.125 inches thick, and will not add appreciable thickness to the coil assembly. However, the tape is depicted as being more substantial for ease of illustration.

As previously noted, although the bundles of turns may be formed to be substantially square as shown in FIG. 4D, they may be bundled so that they are substantially circular instead. For instance, consider a bundle having five turns. One turn may be positioned generally within the middle of the bundle with the remaining four turns surrounding this centrally-positioned turn. The resulting bundle may be substantially circular rather than square.

Figure 5A:
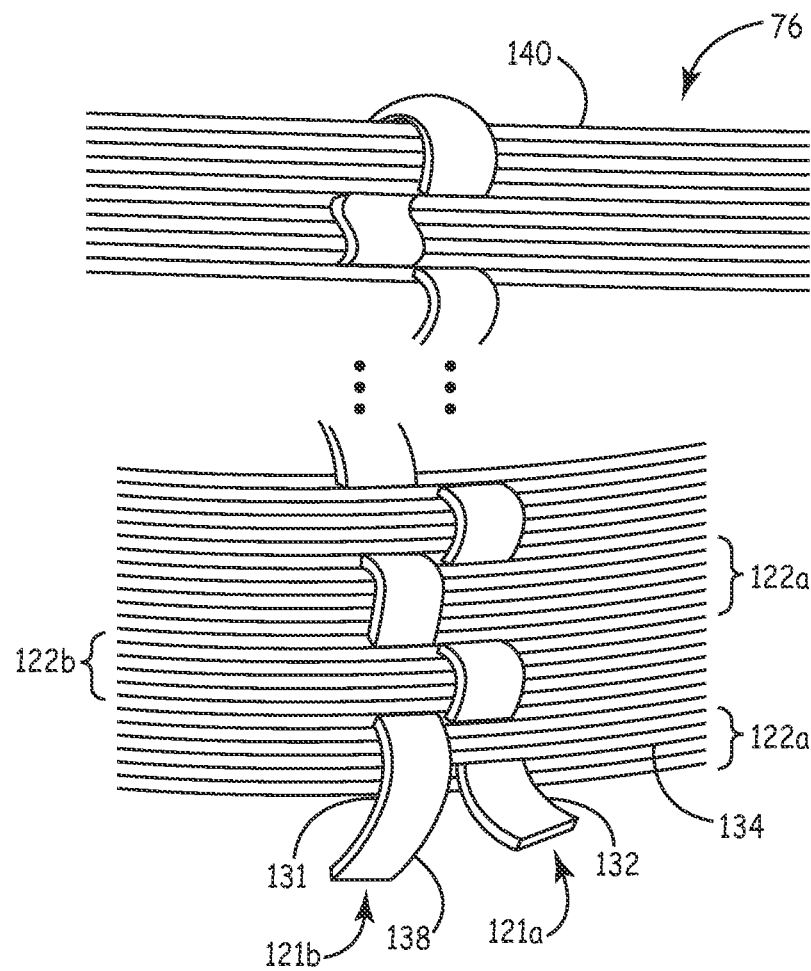
FIG. 5A is an exploded side view of lacing of the coils of one embodiment.

FIG. 5A is an exploded side view of lacing 131 of FIG. 4D. This view shows how the lacing is woven between adjacent turns of coil 76 to form bundles. For instance, bundles 122a, 122b, and 122c are formed at an outer edge of the coil. Each bundle is formed to have a length and width that is substantially the same dimension as one another and as the desired thickness of the coil. This is as shown in FIG. 4D.

The lacing is woven within row 121a until it reaches an inner edge 140 of the coil. At that point, the lacing is wrapped over the edge 140 and an adjacent row 121b is formed. The ends of the lacing 132, 138 may be tied together, may be wrapped around the outer-most bundle in the manner shown in FIG. 4D, or may be maintained together in some other fashion (e.g., by gluing them, affixing the adhesive surfaces one to another, using a fastening device to affix the ends, and so on.) As may be appreciated, it may be desirable to select the total number of turns of the coil such that each bundle will have the same number of turns and all bundles will therefore be of roughly the same size. For instance, if each bundle is to have "nine" turns, it may be desirable to have some multiple of "nine" total turns. In a specific embodiment, the coil has 120 total turns, which are bundled into twelve groups of 10 turns.

Many alternative embodiments of the aforementioned lacing process may be practiced according to the current disclosure. For instance, in the current example, one strand of lacing 131 is used to form the two rows. In an alternative embodiment, multiple strands may be used to form respective rows. In this case, some fastening mechanism may be used to affix ends of the multiple strands at the inner coil edge as well as at the outer coil edge. In another embodiment, the two rows may be "criss-crossed" so that for adjacent bundles, the two strands change position with respect to each other (i.e., a given strand alternates between being on the left and the right with respect to the other strand). This would form a "crossing" pattern on one face of the coil. If desired, one or more additional rows may be added to a set of lacing. For instance, the set of lacing 120c may be augmented to include more than two rows.

If an injection molding process is used to apply the overmolding material to coil 76, it may be desirable to weave lacing tightly enough so that each bundle is coupled to adjacent bundle(s) such that no visible gaps exist between the bundles. If lacing is too loose and spaces exist between adjacent bundles, material will be injected between bundles during the high-pressure overmolding process, resulting in an antenna that is too rigid.

However, competing interests exist in not weaving the lacing too tightly. If lacing is too tight, adjacent bundles will be coupled too rigidly one to another, resulting in a final antenna structure that is likewise too rigid.

In addition to increasing rigidity of the coil, packing adjacent turns of the coil too tightly will tend to decrease the quality factor, or "Q", of the coil 76. The quality factor refers to the ratio of the reactance of the coil (based on coil inductance and any capacitance at resonance) to the impedance of the coil. The higher the Q factor, the more efficiently the coil can store and transfer energy. When adjacent coil turns are packed together too tightly in the same bundle, or alternatively when bundles are tied too tightly one to another, a "proximity effect" occurs. According to this effect, current in one turn of the coil induces eddy currents in adjacent coil turns. Such eddy currents make the coil perform as though it has a higher impedance, thereby decreasing the Q of the coil 76. However, this proximity effect is localized such that allowing some limited spacing between adjacent turns (that is, not "packing" turns too tightly) will largely decrease this effect, thereby increasing the Q of the coil. For this additional reason, it is not desirable to have adjacent turns that are packed too tightly.

For the foregoing reasons, it is advantageous to allow lacings to be applied so that visible gaps between bundles do not exist when the laced coil structure is lying on a flat surface without any force being exerted to separate adjacent bundles. However, the adjacent bundles should be coupled loosely enough so that when modest pressure is applied to separate adjacent bundles at a point where the lacing is woven, small spaces will appear between bundles in the vicinity of the lacing.

The foregoing assumes that adjacent bundles will be coupled one to another by the woven lacing. As yet another embodiment, each bundle may be created by its own lace (e.g., a separate piece of tape that is not connected to the other bundles). A similar concept would allow more than one, but fewer than all, of the bundles within a row to be created with a separate lacing. Either of these embodiments may allow material to harden between bundles during the molding process, particularly if injection overmolding is used to apply the material. This may result in loss of flexibility of the final antenna structure, as discussed above. Thus, an embodiment that does not couple adjacent bundles one to another may be more appropriately used with a molding process that does not apply material under high pressures.

The embodiment shown in FIG. 4A provides four sets of lacing 120a-120d. More or fewer sets may be provided in the alternative. For instance, six, eight, or ten sets of lacing may be provided. In one embodiment, the sets are equidistant from one another but this need not be the case. While providing additional sets of lacing may increase the overall stability of the coil structure, it may likewise reduce coil flexibility. Increasing the number of sets of lacing may further increase the production cost of the coil.

Figure 5B:
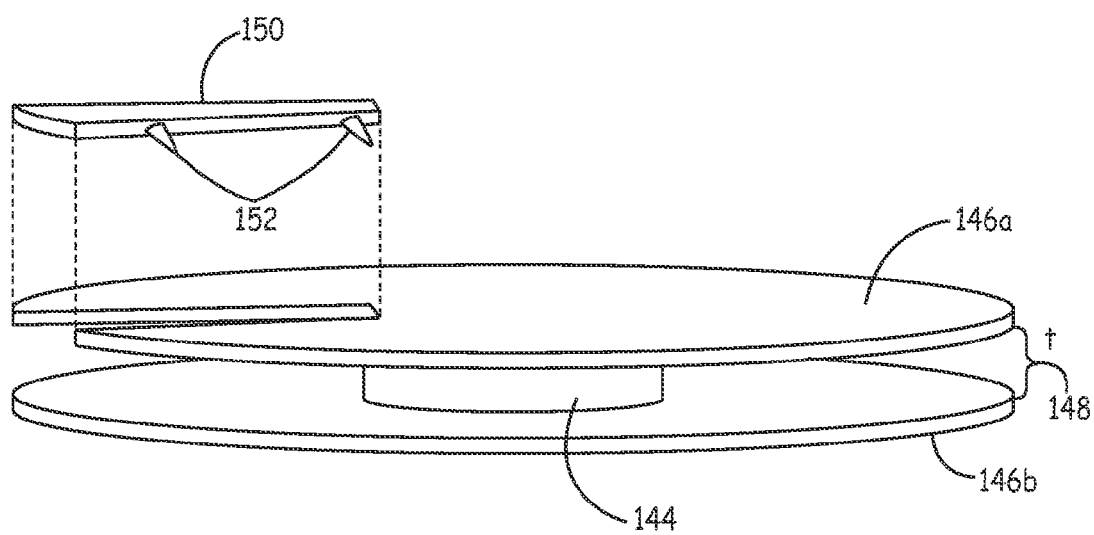
FIG. 5B is a perspective view of one embodiment of a bobbin assembly used to form a coil.

FIG. 5B is one embodiment of a bobbin assembly that may be used for winding a coil as described herein. The bobbin assembly includes a central rod 144 around which a conductor is wound. This rod may be circular or some other shape, such as oblong. The resulting coil will take the shape of the central rod.

Each end of rod 144 is terminated by a respective flange 146a and 146b. The flanges are separated by a distance 148 that is selected to be substantially the desired coil thickness t. As the conductor is wound about this central rod 144 of the bobbin, the flanges force the windings into the space between the flanges so that the resulting coil has approximately the desired thickness t.

In one embodiment, after all turns of the coil are wound around central rod 144, the inductance of the coil may be tested to determine whether it is within some tolerance of a predetermined nominal inductance. In one case, the predetermined inductance is 1.22 millihenries. If the inductance of the coil is not within some tolerance of this predetermined inductance, the total length of the conductor used to form the coil may be adjusted, either by removing a portion of the total length or adding to this total length. This may involve, for instance, removing a portion of a coil turn or adding a partial coil turn.

In one example, at least one of the flanges may have a breakaway portion 150 that may be removed after the coil is wound around central rod 144. Removal of the breakaway portion will expose the windings of the coil so that a set of lacings may be added to the coil. Breakaway portion 150 may include one or more retention members 152, which may be provided on one or both side of breakaway portion 150, and which are designed to hold breakaway portion 150 in place during winding of the coil. For instance, each retention member 152 may be designed to engage, and mate with, a corresponding slot provided within the flange. In one particular embodiment, the retention members may be spring-loaded to flexibly engage the corresponding slots. Many other types of retention members are possible, including clips, clasps, hinges, or any mechanism that would retain breakaway portion 150 in place with respect to flange 146a during the winding process.

If desired, a breakaway portion may be provided for flange 146b at a location roughly corresponding to that of breakaway portion 150 of flange 146a so that both a top and bottom "slice" of the wound coil will be exposed when both breakaway portions are removed. This will allow lacing to be readily woven into the wound coil while the intact portions of flanges 146a and 146b hold the coil in place.

If multiple sets of lacing are to be provided, multiple breakaway portions may be provided for each of flanges 146a, 146b. For instance, a pair of breakaway portions may be provided on flanges 146a and 146b that corresponds to each of the four sets of lacing 120a-120d shown in FIG. 4A. For each set of lacing, a corresponding pair of breakaway portions may be removed, the lacing added, and the breakaway portions returned to the flanges before the next set of lacing is added. This provides maximum stability to the wound coil during the lacing process.

The embodiment of FIG. 5B provides temporary slots formed by removing breakaway portions. In another embodiment, permanent slots are formed within one or more of the flanges. This is shown in reference to FIGS. 5C and 5D.

Figure 5C:
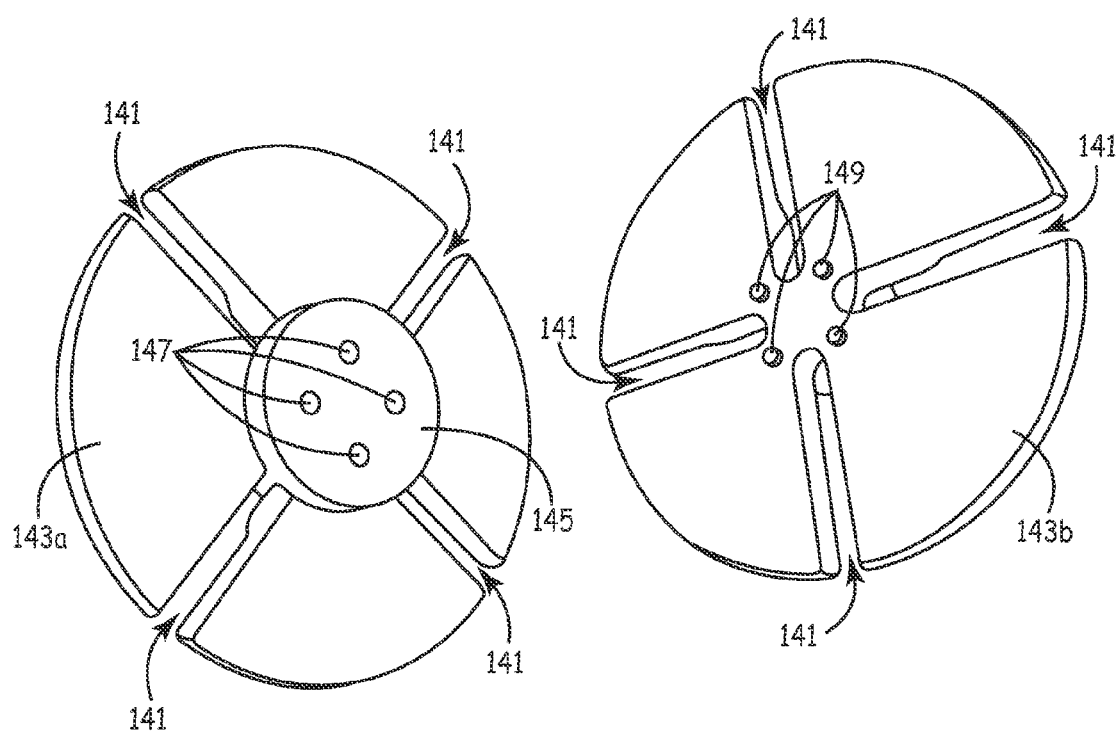
FIG. 5C is a perspective view of another example of a bobbin assembly.

FIG. 5C is a perspective view of two flanges 143a and 143b of a bobbin assembly that have been disconnected one from another. In the example, each of the flanges has four equidistant permanent slots 141, however more or fewer such slots may be used in the alternative to provide for more or fewer sets of lacing. These slots may, but need not be equidistant.

Flange 143a includes a central rod 145 extending therefore. Central rod 145 is adapted to couple to flange 143b via indentations 147 that mate with protrusions 149 of flange 143b. However, many other mechanisms for coupling one flange to another may be employed in other examples. When the flanges 143a, 143b are so coupled one to another, the permanent slots 141 of flange 143a are aligned with those of flange 143b to allow lacing to be added, either after all turns of the coil are wound around central rod 145 or during the winding process. The mechanism for applying lacings during the winding process is discussed further below.

The ability to de-couple flanges 143a and 143b one from another as shown in FIG. 5C allows a coil wound around central rod 145 to be easily removed after the winding process is complete and lacings have been added.

Figure 5D:
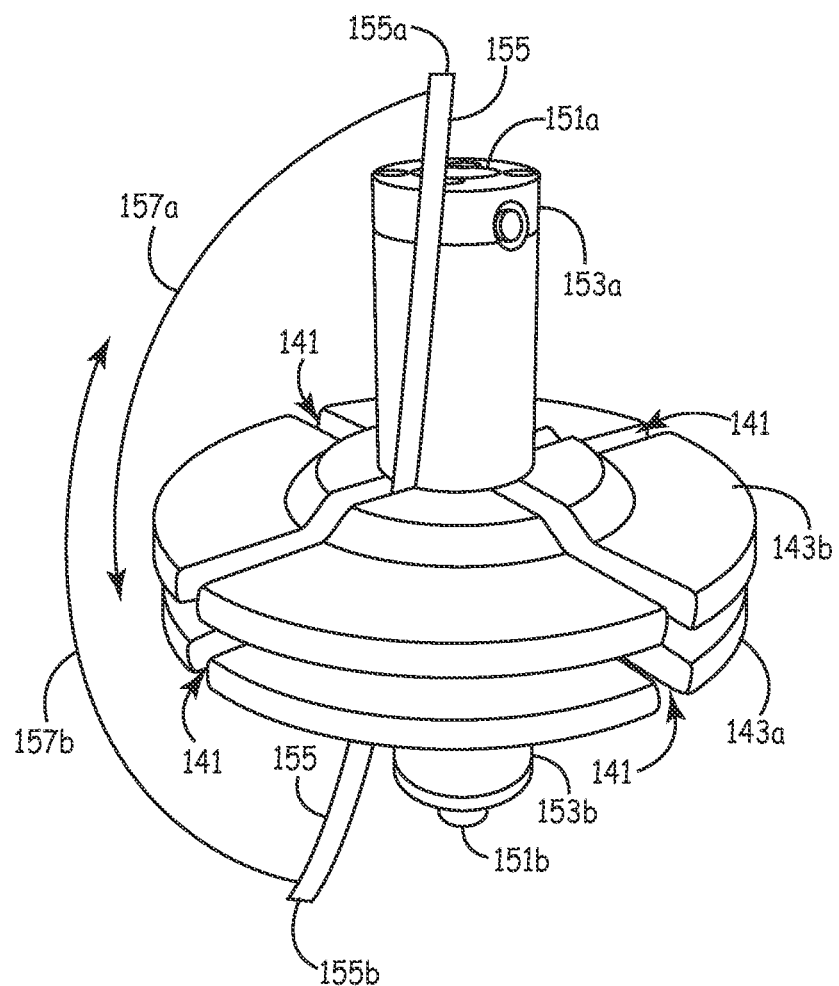
FIG. 5D is another view of the bobbin assembly of FIG. 5C.

FIG. 5D is a perspective view of flanges 143a and 143b when they are coupled one to another. This view illustrates the manner in which permanent slots 141 of flange 143a are aligned with those of the other flange 143b to allow four sets of lacing to be applied to a coil that is wound around central rod 145 (FIG. 5C).

The actual winding process may be performed by affixing the bobbin assembly of FIG. 5D into a larger winding machine. For instance, a rod of the larger winding machine (not shown in FIG. 5D) may be received by a channel 151a provided in rod 153a. Similarly, a mating element 151b in rod 153b may interface with an opposing element of the winding machine (not shown). Many mechanisms may be contemplated for affixing the bobbin assembly of FIG. 5D into a winding machine, and those illustrated are examples only. The winding machine may then control the coil winding process, including rotating the bobbin assembly at a predetermined speed to wind a conductor around central rod 145 using a predetermined controlled tension. Such a winding process may be controlled automatically (e.g., by control circuitry programmed in a desired manner) or by an operator who may be controlling, at least in part, the winding machine via manual mechanisms (e.g., a foot pedal).

The bobbin assembly of FIG. 5D may be used to apply lacings after all of the turns of a conductor have been wound around central rod 145 in a manner described above. For instance, 120 turns may be wound around central rod 145 and thereafter lacings may be woven into coil at the openings provided by slots 141. In another embodiment, the lacings are added during the winding process.

As one example of applying lacing during the winding process, a lacing (e.g., a predetermined length of flexible tape) may be threaded through each of slots before any turns of the coil have been wound around central rod 145. An example lacing 155 is shown threaded through one of the pairs of slots 141 so the lacing is substantially parallel with rods 153*a*, 153*b*, and central rod 145 (not visible in this view). If tape is used for lacing 155, an adhesive provided on the tape may, in one example, be used to maintain the lacing in position against rods 153*a*, 153*b*, and central rod 145 before, and while, a conductor is being wound around central rod 145.

After a corresponding lacing has been threaded through each of the four slots and positioned in a manner similar to that shown for lacing 155, a first set of conductor turns may be wound around central rod 145 between flanges 143*a*, 143*b*. This first set of conductor turns may comprise the number of turns to be included in one bundle (e.g., ten turns of the coil in one specific example). Thereafter, the winding process may be temporarily halted and the two opposing sides of lacing 155 may be used to retain the conductors in a bundle. This may be accomplished, for instance, by rotating each end of the lacing through a corresponding slot to the other slide of the bobbin assembly. As a specific example, force may be exerted on end 155*a* of lacing 155 to rotate the corresponding side of the lacing in a direction generally indicated by arrow 157*a*. In this manner, the lacing may be slid through the corresponding pair of slots 141 to a position shown occupied in FIG. 5D by end 155*b* of lacing. Similarly, end 155*b* of lacing 155 may be rotated in a direction generally indicated by arrow 157*b* so that the corresponding side of the lacing slides through the pair of slots 141 and into a position previously occupied by end 155*a*. The first bundle of turns is thereby created by the crossing of the two opposing sides of the lacing 155. If desired, a knot may be tied in lacing to maintain lacing in a snug position around bundle rather than by merely crossing the two ends 155*a*, 155*b* to create each bundle.

As discussed above, it may be desirable in one example to create bundles that are "snug" but not overly tight. This will increase the Q of the coil and also allow the coil to be more flexible. To accomplish this, after opposing sides of lacing are crisscrossed, ends 155*a*, 155*b* are pulled just until they are tight without exerting any further force that would otherwise stretch or break the lacing (e.g., stretch the tape). Once the ends of the lacing are pulled taunt, no additional force need be exerted to pull the lacings any tighter to thereby compact the bundles any further.

Although only one lacing 155 is shown in FIG. 5D, it will be appreciated that a lacing may be provided for each pair of slots (e.g., four in this example), and a similar process is performed for each such lacing. Thus, the process may be performed four times for the example shown in FIG. 5D for each set of conductor windings.

After all sets of lacings are "crisscrossed" from one side to another, adhesive carried by the lacings may be used to affixed the sides of the lacing to rods 153*a*, 153*b* so that the sides of the lacings are out of the way as additional turns of the conductor are wound around the bobbin assembly. For instance, after crisscrossing of the ends of lacing 155, the side associated with end 155*b* may be affixed to rod 153*a*, and the side associated with end 155*a* may be affixed to rod 153*b*.

Next, another set of conductor turns (e.g., another ten turns) may be wound around central rod 145. Thereafter, each side of a lacing is again moved through the correspond pair of slots 141 to the other side of the bobbin assembly to form yet another bundle. This process may be repeated any number of times to create a desired number of bundles. As a specific example, this process may be performed twelve times to create twelve bundles. After the final (that is, the outer) bundle is created, the ends of lacing may be tied around the this last bundle to allow the ends to be permanently affixed one to another, if desired. Alternatively, some other mechanism such as an adhesive may be used to affix opposing ends of the lacing. Any loose ends may be trimmed to a final length.

In the foregoing manner, lacings may be applied to form a bundle after each set of conductor turns is wound around central rod 145. This may be more efficient, and could be more readily automated, than a process that performs the weaving after all turns of the conductor have been wound around central rod 145.

Variations of the weaving process are possible. For instance, rather than crossing each end of lacing through a corresponding pair of slots 141 to the other side of the bobbin assembly, the two sides of the lacing may simple be brought together, twisted around one another, and then returned to their original side of the bobbin assembly. For example, first and second ends 155*a*, 155*b* may be grasped to extend both sides of lacing outward radially from rods 153*a*, 153*b* (e.g., thereby allowing the two opposing sides of the lacing, including the two ends, to extend substantially perpendicularly from rods 153*a*, 153*b* and central rod 145). In this case, the two sides of lacing 155 may be positioned roughly in the middle of the pair of slots. When so positioned, these two sides of the lacing may be twisted one or more times around one another. Each of the ends 155*a*, 155*b* may then be returned to their respective original positions shown in FIG. 5D. Slight force may be applied to both ends so that both sides of the lacing are taunt, thereby creating a "half-knot" around the conductor turns that will bundle together these associated turns. If desired, this half-knot could instead be replaced by a full-knot. In either of these examples, the two sides of the lacing 155 need not be crisscrossed (e.g., so that ends 155*a* and 155*b* "switch sides" of the bobbin assembly) to complete the weaving process. Thus, many variations are available for weaving lacings in a manner that creates bundles of adjacent turns of coil 76.

In any of the foregoing embodiments, after each bundle is formed, each of the two sides of lacing 155 may be affixed again to a respective one of the rods 153*a*, 153*b* in preparation for bobbin assembly to receive a next set of windings. This can be accomplished by adhesive on the lacing, as when using single- or double-sided tapes.

As discussed above, it is desirable for the bundles to have a length and width that are the same as the desired thickness of the coil. In examples of the weaving processes described in reference to FIGS. 5C and 5D, the created bundles will tend to have a circular cross-section. In this case, the diameter of the cross-section should be selected to be the desired coil thickness. This can be controlled by selecting an appropriate type of conductor (e.g., a type of Litz wire having a certain cross-section) as well as by selecting the number of turns of the conductor to include in each bundle.

In other cases, bundles may take a more rectangular shape, with the assumed shape being affected by such factors as a total number of turns in a bundle and type of conductor being bundled. In this case, as well as the foregoing case, the length and width of the bundles will again be determined by selecting an appropriate type of conductor (e.g., having a certain cross-section) as well as by selecting the number of turns of the conductor to include in each bundle. The bundles should generally have a length and width that are substantially the same, and which are the same as the desired thickness of the coil.

The foregoing discussion focuses on winding of the coil 76. Next, a circuit assemble is disclosed that may be used in one embodiment of a coil 76. Such a circuit assemble may be employed, for instance, to carry a capacitor such as tuning capacitor 96. Allowing the coil 76 to carry the tuning capacitor 96 rather than placing this capacitor with other circuit components in circuit module 110 may provide advantages, such as allowing the high-voltage node between the tuning capacitor 96 and coil 76 to be carried within the well-protected and insulated structure of antenna 78. This minimizes the chance that the patient will come in contact with this node.

Figure 6A:
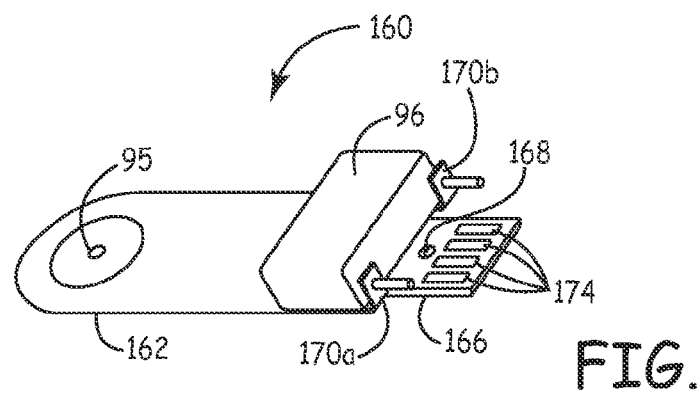
FIG. 6A is a perspective view of a circuit assembly of one embodiment that may carry a tuning capacitor and/or a temperature sensor.

FIG. 6A is a perspective view of a circuit assembly 160 to carry tuning capacitor 96 and a temperature sensor 95, which may be a thermistor. Circuit assembly 160 includes a flexible substrate 162 that may be formed of any type of flexible material such as a polyimide tape, including Kapton® high-temperature polyimide tape. As discussed above, Kapton tape has a pressure-sensitive adhesive backing that will allow substrate 162 to remain in position relative to coil 76 during the overmolding process. Another type of suitable tape includes FEP Teflon® film Circuit assembly 160 may further include a stiffening member 166, which is a substrate that is thicker and substantially more rigid than flexible substrate 162. Stiffening member 166 may be made of standard circuit board materials, including epoxy laminates such as FR-4. The stiffening member may include an aperture 168 that will be mechanically coupled to a strain relief member of cable portion 112b (FIG. 3) as will be discussed further below. Force exerted on cable 112 will be transferred to the strain relief member rather than being exerted on electrical conductors carried by cable 112. In an alternative embodiment wherein strain relief is not needed, stiffening member may be eliminated.

In the illustrated embodiment, substrate 162 and stiffening member 166 carry tuning capacitor 96, which may be a high-temperature, high VAC wound capacitor. This type of component is commercially-available from EPCOS AG. The value selected for the capacitor is largely dependent on the inductance of coil 76 and the target frequency at which coil 76 will be driven. In one embodiment wherein the target resonant frequency is about 41 KHz, the capacitance is selected to be about 12 nF.

Tuning capacitor 96 may be mechanically-coupled to substrate 162 via tabs 170a and 170b. This capacitor may further be electrically-coupled to pads 174 provided by stiffening member in such a manner that the capacitor is connected in series with coil 76. For instance, one of the ends 118a and 118b of coil 76 (FIG. 4A) may be electrically and mechanically coupled to one of the pads 174 while the other end is coupled to a terminal of capacitor 96. The other terminal of the capacitor may then be coupled to a different one of pads 174, thus configuring the coil and capacitor to be electrically in-series. The two pads 174 that are so coupled may then be driven by coil interface 82 (FIG. 2) during recharge operations.

Flexible substrate 162 also carried temperature sensor 95, which in one embodiment is a thermistor. For instance, a thermistor may be selected that is resin coated to provide good mechanical strength and resistance to solvents. A thermistor may be selected that has high-resolution over at least a portion of its operational temperature range. In one scenario, the thermistor has a high-resolution range that is accurate to within 0.1° C. over a temperature range spanning 30° C. to 50° C. Another embodiment expands this high-resolution range to 0° C. to 70° C. An example component that may be selected as a thermistor includes the SC30 thermistor commercially-available from the GE Corporation.

Temperature sensor may include multiple terminals to provide signals indicative of temperature. These terminals may be electrically coupled via traces carried by substrate 162 to respective ones of pads 174 of stiffening member 166. As discussed above, in an alternative embodiment wherein stiffening member 166 is not needed, pads 174 coupled to temperature sensor may instead be carried by flexible substrate 162. In still another scenario, flexible substrate 162 may be eliminated and all components, including temperature sensor 95, may be carried by stiffening member 166.

Figure 6B:
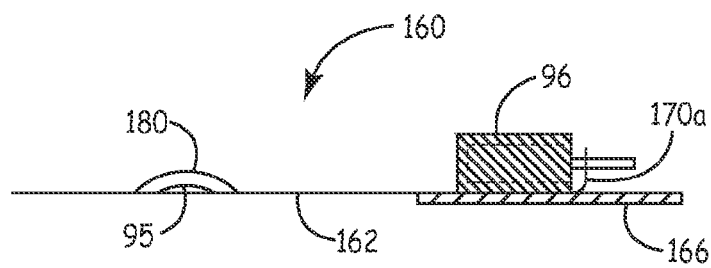
FIG. 6B is a side view of the circuit assembly.

FIG. 6B is a side view of circuit assembly 160, including flexible substrate 162, stiffening member 166, tuning capacitor 96, and temperature sensor 95. This view depicts the manner in which the flexible substrate 162 is placed over a portion of stiffening member 166. In one embodiment wherein the flexible substrate is adhesive polyimide tape, this positioning is maintained by pressing the adhesive surface of the tape against stiffening member 166.

Temperature sensor 95 of one embodiment is encapsulated in a protective bubble 180 that may be formed of a heat-resistant resin that become solid after it is applied over the temperature sensor 95, and thereafter will not melt during the overmolding process. This protective bubble 180 holds temperature sensor 95 in place on flexible substrate 162 and further protects the temperature sensor from outside forces that may be exerted on antenna 78.

Figure 6C:
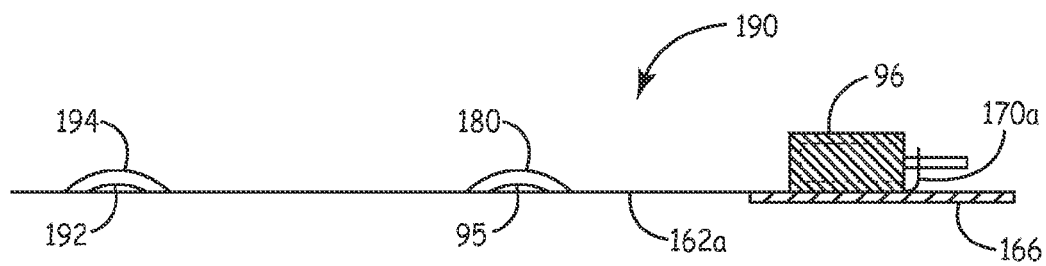
FIG. 6C is a side view of another circuit assembly embodiment.

FIG. 6C is a side view of another circuit assembly 190 that may be used in one embodiment. This circuit assembly is similar to circuit assembly 160, and similar components are labeled with like numeric designations. For instance, circuit assembly may optionally include a stiffening member 166, and may carry a tuning capacitor 96. However, in this scenario, flexible substrate 162a of FIG. 6C is longer than substrate 162 of FIGS. 6A and 6B. Substrate 162a carries an additional temperature sensor 192, which may be similar to temperature sensor 95. Like temperature sensor 95, temperature sensor 192 may be encapsulated in a protective bubble 194. Terminals of temperature sensor 192 may be coupled to additional ones of pads 174 in a manner similar to that described above with respect to temperature sensor 95. The positioning of circuit assembly 190 relative to coil 76 will be discussed further below.

Figure 6D:
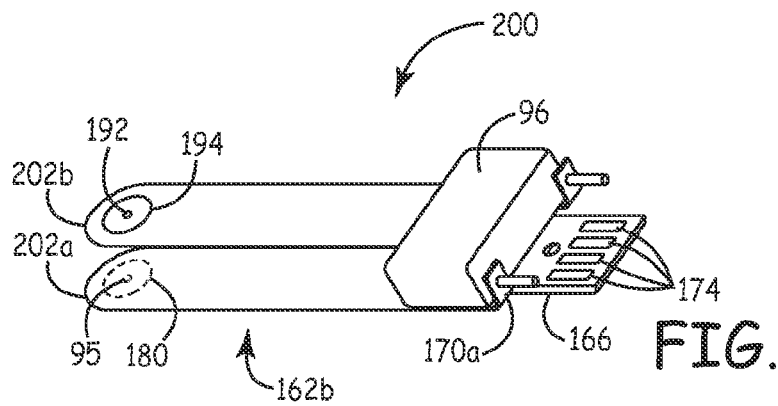
FIG. 6D is a perspective view of another circuit assembly embodiment.

FIG. 6D is a perspective view of yet another circuit assembly 200 that may be used in one embodiment. This circuit assembly is similar to circuit assembly 160, and similar components are labeled with like numeric designations. For instance, circuit assembly may optionally include a stiffening member 166, and may carry a tuning capacitor 96. However, this embodiment includes a flexible substrate 162b which includes two independent finger-like appendages 202a and 202b that are separately-positionable relative to coil 76, as will be discussed below. Each such appendage carries a respective one of temperature sensors 95 and 192, each covered by an associated protective bubble, 180 and 194. Temperature sensor 95 and associated bubble 180 (shown dashed) may be located on a surface away from appendage 202b (not visible in this drawing) and the other temperature sensor 192 and bubble 194 may be located on a surface of appendage 202b away from appendage 202a (that is, the top, or visible side, of appendage 202b in this figure). This will prevent the "bumps" resulting from the sensors from interfering with the way appendages 202a and 202b contact the coil, as will be discussed below. When an additional temperature sensor 192 is incorporated into circuit assembly 200, stiffening member 166 or substrate 162 may include additional pads 174 to be electrically-coupled to the terminals of the additional sensor.

Figure 7A:
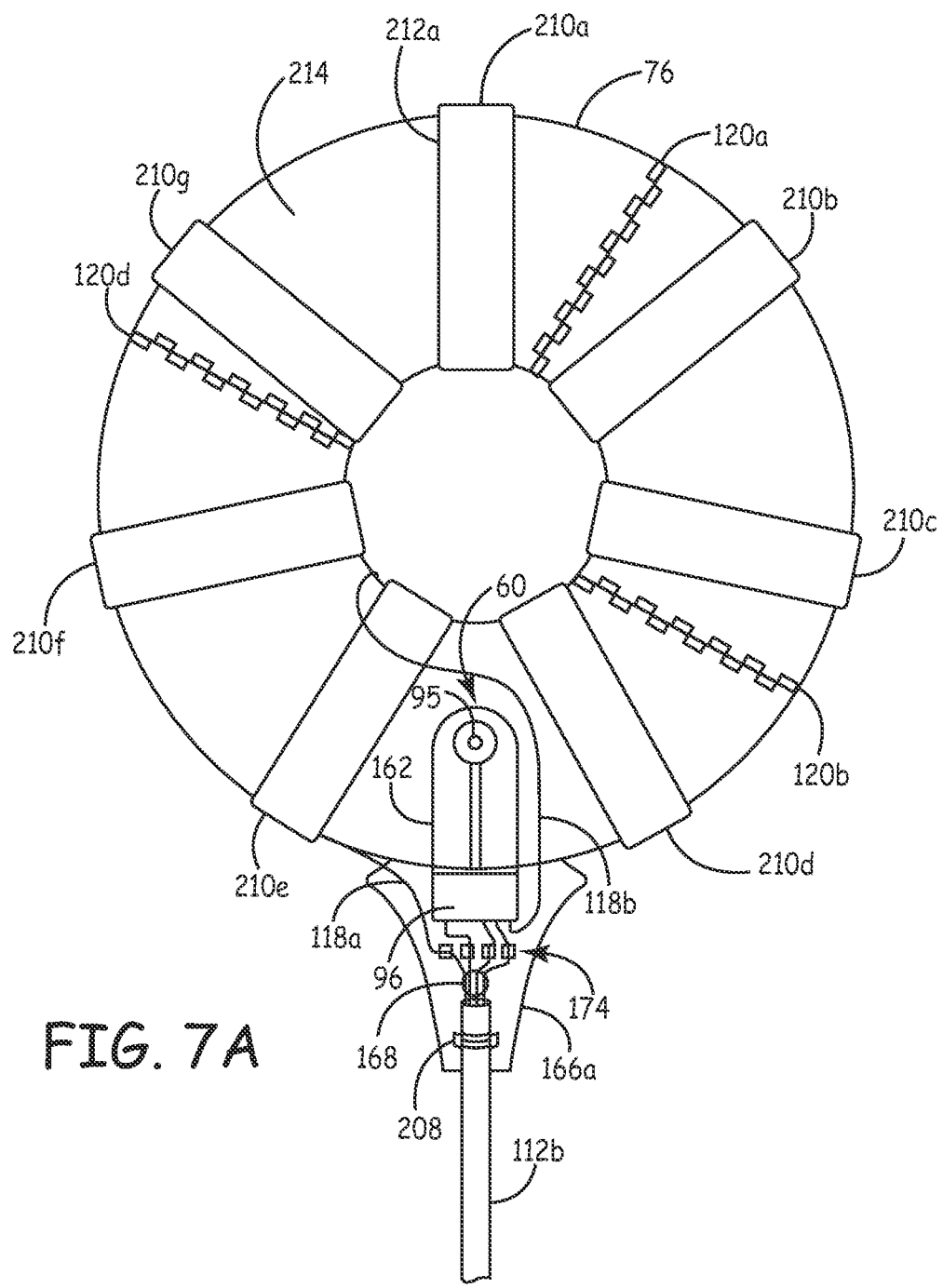
FIG. 7A is a top view of one embodiment of a coil after a first shot of material is applied.

FIG. 7A is a top view of coil 76. In this view, flexible substrate 162 has been positioned on top of coil 76. As shown in FIG. 7A, temperature sensor 95 may be positioned midway between the outer and inner edge of the coil. This may provide an optimal temperature indication of the antenna during recharge. Flexible substrate 162 may be formed around the outer edge of the coil 76 so that tuning capacitor 96 and stiffening member 166b are not aligned with temperature sensor (which are sitting a bit above the coil surface), but rather are substantially in-line with the coil, as will be discussed below. This helps maintain a thin antenna profile, since the thickness of the capacitor housing, or "can", is not stacked on top of the coil.

In FIG. 7A, stiffening member 166a has a different form factor than stiffening member 166 that is shown in FIGS. 6A-6D, having a longer body adapted to support a terminal end of cable portion 112b, and having a flared configuration on either side to encircle a portion of coil 76. This provides a larger surface area to support ends 118a, 118b of coil 76. As discussed above, one end of coil, shown as end 118a, may be electrically and mechanical coupled to one of pads 174 while the other end 118b is coupled to a terminal of tuning capacitor 96. The other end of tuning capacitor may be coupled to another one of the pads 174, placing the coil and capacitor electrically in-series between those two pads. Other ones of the pads may be coupled to terminals of temperature sensor 95. Each of pads 174 may further be electrically-coupled to a corresponding conductor carried within cable portion 112b.

In the one embodiment, stiffening member includes an aperture 168 to receive a strain relief member of cable 112b. For instance, the strain relief member may be a portion of the nylon serving carried within cable 112b. This strain relief member is inserted into aperture 168 and affixed to stiffening member so that forces exerted on cable portion 112b will be transferred to strain relief member and will not cause failures in the electrical connections of the system. Additional support may be provided by a collar 208 that is adapted to retain an end of cable portion 112b in place with respect to stiffening member 166a. If desired, support and strain relief may be provided for the coil ends 118a and 118b by employing shrink-wrap tubing to encircle and protect these ends.

In yet another embodiment, the length of substrate 162 may be extended towards, or even encircle, the inner edge of coil 76. A conductive trace carried by this extension may be used to terminate end 118b near the inner edge of the coil, eliminating the need to wrap the cable end 118b over coil and towards the outer edge of the coil.

FIG. 7A further illustrates coil 76 after it undergoes a first-shot of a two-shot injection molding process that is used to form antenna 78 according to one example. In particular, the first shot is used to form multiple spokes 210a-210g, each encircling a respective portion of the front and back surfaces of coil 76, as well as respective portions of the inner and outer edges of the coil. These spokes have a substantially uniform thickness around the coil, such that the top surface 214 of coil 76 is located substantially the same distance from the top surface of a spoke as the bottom surface of the coil (not visible in FIG. 7A) is located from the bottom surfaces of a spoke. For instance, the distance between top surface 214 of coil 76 and top surface 212a of spoke 210a is substantially the same as the distance between the opposite (or bottom) surface of coil 76 and the opposite (or bottom) surface of spoke 210a (with the bottom of the coil and spokes being visible if the assembly were "flipped over" as compared to the view shown in FIG. 7A.) The coil 76 is thereby "sandwiched" at a location that is equidistant from the top and bottom surface of the spokes. These spokes will serve as retention members during a second-shot molding process, as will be discussed below.

Many different insulating materials may be used to form spokes 210 (as well as the rest of the structure that comprises the antenna molding. Various types of polymers, including silicones, polypropylene, and urethanes may be used for this purpose. Ideally, the selected material should be tough, strain resistant, light weight, water resistant, flex resistant (i.e., it will not crack or become damaged upon repeated flexing), have the ability to withstand temperatures somewhat over 41° C., and present a pleasing texture. In one embodiment, CoolPoly® thermally-conductive elastomer is selected for this purpose. This polymer, which is available from Cool Polymers, Inc., has a thermal conductivity of 3 W/mK, allowing heat dissipated during recharging to be spread more evenly throughout antenna 78, thereby providing a more comfortable recharge experience for the patient. In a particular embodiment, the CoolPoly elastomer that is selected has a hardness of 45 Shore A.

While the view of FIG. 7A shows retention members taking the form of spokes 210a-210f, the retention members may take virtually any other format so long as, in one embodiment, the distance between top surface 214 of coil 76 and the top surface of a retention member is substantially the same as the distance between the opposite (or bottom) surface of coil 76 and the opposite (or bottom) surface of a retention member. This will result in coil 76 being maintained mid-way between the top and bottom surfaces of the retention member, and therefore centered within a second-shot mold during the second-shot molding process, as will be discussed below. In this embodiment, the finished antenna will be "bi-directional", as discussed above, providing benefits during recharge such as ease of use.

Figure 7B:
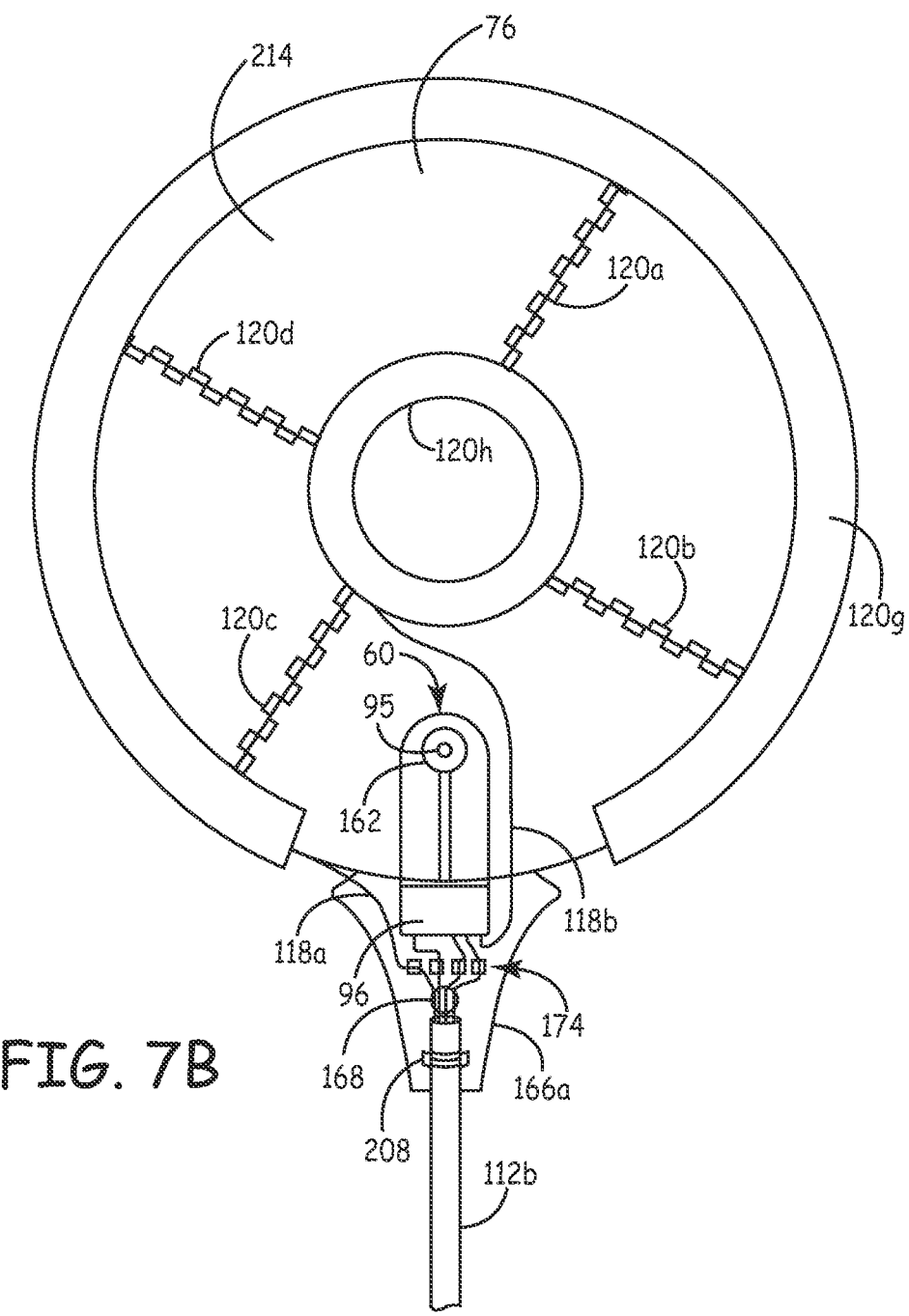
FIG. 7B is a top view of another embodiment of a coil after a first shot of material is applied.

FIG. 7B is a top view of coil 76 illustrating retention members 120g and 120h that are in a format other than radiating spokes as shown in FIG. 7A. In this view, elements similar to those shown in FIG. 7A are labeled with like numeric designators. This embodiment includes a first retention member 120g formed around a portion of the outer circumference of coil 76. While not shown in this view, the retention member is formed around the outer edge of coil 76 so that this member will appear substantially the same if the assembly is "flipped" to reveal the other major surface of the coil. Likewise, a second retention member 120h is formed around the inner circumference of coil 76, and will appear substantially the same if the coil assembly is flipped. These retention members will maintain the coil in the middle (e.g., in relation to coil thickness) of a second-shot mold during a second-shot molding process, as will be discussed below. This will allow the resulting coil assembly to be bi-directional.

In yet another embodiment, retention members may take the form of wedges extending from the outer to the inner circumference of coil 76. Alternatively, radiating spokes may be added to interconnect retention members 120g and 120h of FIG. 7B to increase stability of the structure. Many other configurations may be contemplated by those skilled in the art.

While the retention members may be symmetrical so that the coil assembly appears the same from the top or bottom views, this need not be the case. For instance, it is not necessary that the width of retention member 120g is the same when viewed from the top and the bottom. Specifically, retention member 120g may extend a first predetermined distance from the outer circumference of coil 76 on top surface 214 of coil, but may only extend half as far from the outer edge on the opposite side of the coil, as viewed by "flipping" coil assembly to rest on its other major surface. It is only important that the thickness of the retention member be the same relative to the top and bottom surfaces of the coil 76 so that the thickness of the coil is substantially centered within the thickness of the retention members. This will be illustrated by remaining ones of the drawings.

As may be appreciated, virtually any other configuration imaginable may be used for the retention members so long as a distance between the top surface 214 of coil 76 and a top surface of a retention member is substantially the same as a distance between the opposite (or bottom) surface of coil 76 and the opposite (or bottom) surface of a retention member. In one embodiment, it is also desirable to form the retention members so that a portion of the coil 76 that is to be coupled to cable 112b remains exposed so that the mechanical and electrical connections may be created after the first-shot of material is applied. In another embodiment, these connections may be formed before the first shot of material is applied, in which case the need to allow specific portions of the coil assembly to remain accessible is not as critical.

FIG. 8 is a perspective view of antenna 78 following application of the second shot in the two-shot injection molding process. The resulting structure may, in one embodiment, include a central opening 114 that may decrease the thermal mass of the antenna, thereby allowing for better heat dissipation, and making the structure more light weight, as previously discussed. If desired, this aperture need not be provided, as may be desirable if one or more of the elements shown carried by circuit assembly 160 are to instead be located within the inner circumference of coil 76. For instance, a substrate and stiffening member could be located within this area, in which case it may be desirable to enclose the center of the antenna to provide support and protection for these circuit elements.

One embodiment of antenna 78 is formed with ribs on one or both major surfaces of the antenna. During recharge, these ribs contact a patient's skin to help with heat dissipation and increase patient comfort. In another embodiment, more or fewer such raised portions may be provided, and these portions may take other shapes and sizes. For instance, raised "rings" may be provided that encircle all, or a portion of, the center of the coil. Many variations are possible.

Antenna 78 of one embodiment includes a transition portion 224 that narrows where antenna 78 contacts cable portion 112b. This provides a transition region having a flexibility that lies somewhere between the flexibility of the main body of antenna and the flexibility of cable portion 112b to aid in strain relief.

As discussed above, according to one process, antenna 78 is the result of a two-shot injection molding process, wherein the first shot produces spokes 210 of FIG. 7. In preparation for the second shot, the assembly of FIG. 7 is placed in the final mold, with spokes centering coil 76 mid-way between the two major surfaces of this mold. After the second shot is applied, the center of coil 76 will be centered midway between surface 226 of antenna 78 and the opposite surface of antenna (which is viewable if antenna is "flipped over" as compared to the orientation shown in FIG. 8.) The resulting antenna assembly is therefore "bi-directional", meaning coil 76 is substantially equidistance from either of the major surfaces, or faces, of antenna 78. Assuming ribs 222 are provided on the opposite surface, the antenna will look, feel, and perform substantially the same regardless of which surface is positioned against the patient during recharge. This makes the antenna easier to use, since the patient is not burdened by determining a proper antenna orientation prior to performing recharge.

Figure 9A:
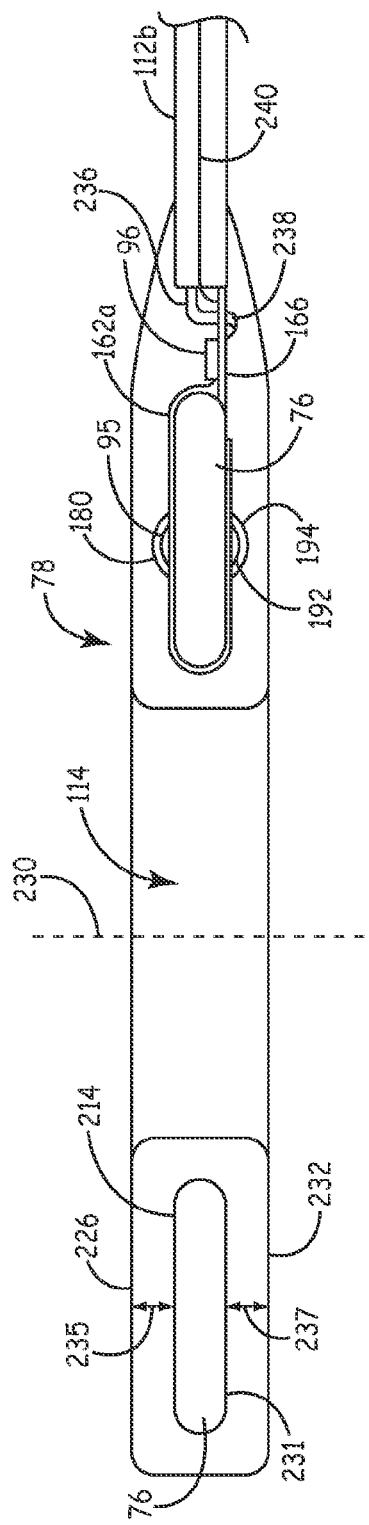
FIG. 9A is a cross-sectional view of one embodiment of an antenna taken at a plane in which resides a central axis of a coil and that is perpendicular to a plane that carries the antenna.

FIG. 9A is a cross-sectional view of antenna 78 at a plane in which resides a central axis 230 of coil 76 and which is perpendicular to a plane that carries the antenna 78. This view illustrates coil 76 being centered such that a top surface 214 of coil 76 is substantially the same distance from top side 226 of antenna as the bottom surface 231 of coil is from the bottom surface 232 of antenna, as represented by arrows 235 and 237, respectively. This provides a bi-directional coil configuration that will allow recharge to be performed with substantially the same coupling coefficient between coil 76 and secondary coil 56 regardless of which side of the antenna is positioned closed to cutaneous boundary 77 of the patient.

FIG. 9A further illustrates an antenna embodiment that employs circuit assembly 190 of FIG. 6C. In particular, flexible substrate 162a is shown wrapped around an inner edge of coil 76. A first temperature sensor 95 is positioned approximately in the middle of the coil surface between an outer and inner edge of the coil. A second temperature sensor 192 is positioned at about the same location on the opposite (bottom in this view) side of the coil. This configuration allows temperature sensing to occur for both surfaces of coil 76 so that a similar temperature measurement may be obtained during recharge regardless of which surface of coil is positioned closest to the cutaneous boundary of the patient.

This figure further illustrates the manner in which tuning capacitor 96 and stiffening member 166 are positioned substantially behind, and in-line with, coil 76 to minimize the profile of antenna 78. Further, in this view, a strain relief member 236 is visible. As discussed above, this strain relief member may be a portion of serving material that is carried by cable portion 112b. Such serving material may be made of nylon or some other material that is preferably an electrical insulator and exhibits adequate strength characteristics. In one embodiment, an end 238 of this strain relief member 236 may be inserted through aperture 168 (FIG. 6A) of stiffening member 166 and maintained in position with epoxy. Other fastening mechanisms may be used to attach strain relief member 236 to stiffening member 166 in the alternative. FIG. 9A further illustrates conductors 240 carried by cable portion 112b that may be electrically and mechanically coupled to conductive pads 174 in the manner described above (FIG. 6A).

Figure 9B:
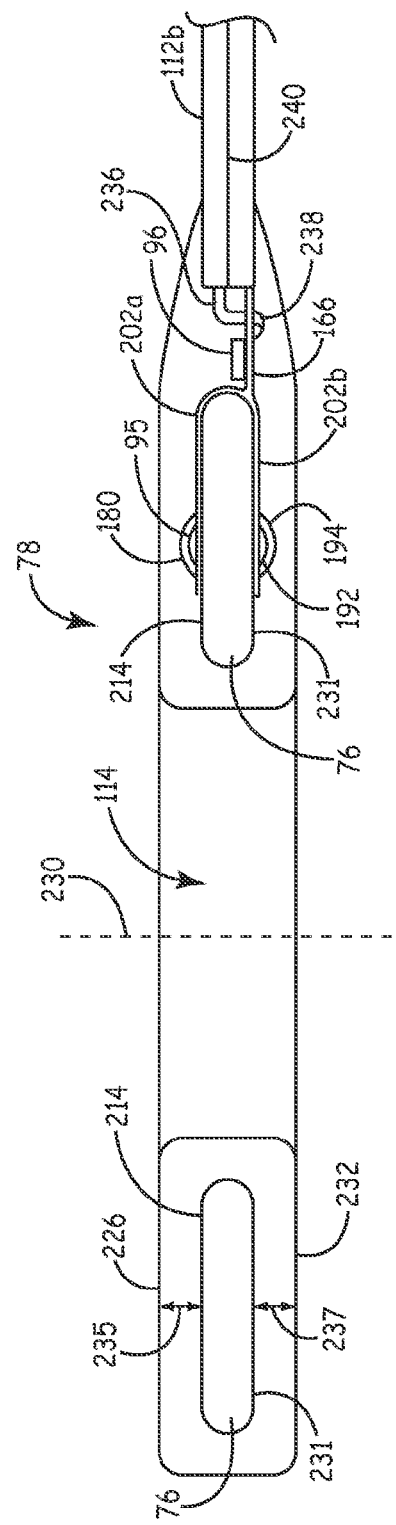
FIG. 9B is a cross-sectional view of one embodiment of an antenna that is similar to the view of FIG. 9A.

FIG. 9B is a cross-sectional view of antenna 78 that is similar to the view of FIG. 9A, and includes similar elements that are denoted with like numeral designations. As shown by FIG. 9B, coil 76 is located substantially within the center of antenna in a manner described above with respect to the embodiment of FIG. 9A.

The embodiment of FIG. 9B differs from that of FIG. 9A in that it includes circuit assembly 200 of FIG. 6D. First appendage 202a of this circuit assembly 200 has been positioned on the top surface 214 of coil 76 while second appendage 202b has been positioned on the bottom surface 231 of coil. As such, temperature sensor 95 is positioned proximate top surface 214 of coil 76 while temperature sensor 192 is positioned proximate bottom surface 231 of coil 76. Since temperature sensor 95 is carried by a top surface of appendage 202a while temperature sensor 192 is carried by the bottom side of appendage 202b (FIG. 6D), appendages 202a and 202b lie flat against, and in one embodiment adhere to, a respective side of coil 76. The respective protective bubbles 180 and 194 protrude away from the surface of the coil. The positioning of the temperature sensors in this manner allows either major surface 226 or 232 of antenna to be positioned against the patient while obtaining similar temperature measurements that can be employed to control recharge operations.

A coil made according to techniques described herein exhibits superior flexibility while also be durable and flex-resistant. In one preferred embodiment, the resulting antenna structure has a thickness of between 0.075 and 0.30 inches and a stiffness of between 2 to 10 pounds per inch. In a more specific embodiment, the primary coil has a thickness between 0.1 inches and 0.165 inches and a stiffness of between 3 to 7 pounds per inch. In a particular embodiment, the coil is about 0.118 inches thick and has a stiffness of about 5 pounds per inch.

Figure 10A:
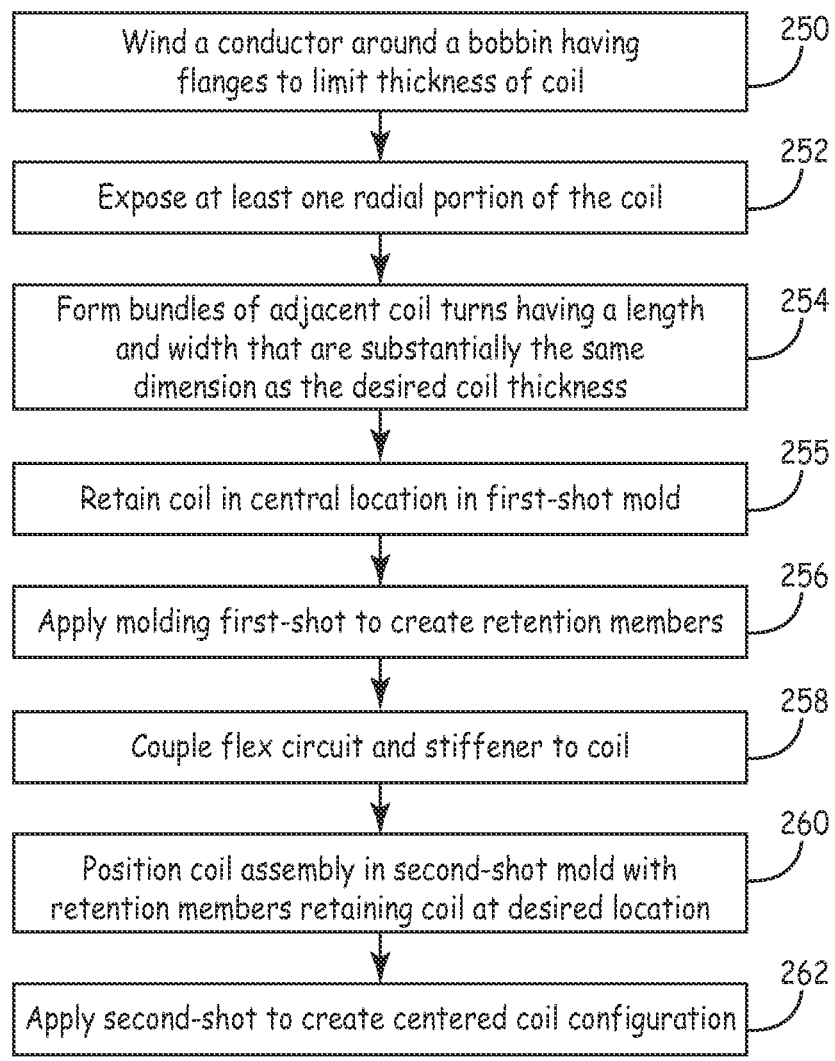
FIG. 10A is one example process of making an antenna assembly according to aspects described herein.

FIG. 10A is one example process of making an antenna assembly according to aspects described herein. A conductor is wound around a bobbin assembly designed to limit the thickness of the coil (250). As discussed above, thickness is limited by two flanges or plates that are located on either end of the central rod of the bobbin. The flanges are spaced apart a distance that corresponds substantially to the desired thickness of the coil. As the conductor is wound about the central rod, the flanges force the windings into a space having the desired thickness, which, in one embodiment, is not greater than 0.165 inches. Other coil thicknesses may be used in the alternative.

Next, in one example, at least one radial portion, or "slice", of the wound coil may be exposed (252). The exposed portion will correspond to an area of the coil that is to receive a set of lacing. Exposing a slice of the coil may be accomplished by having a break-away portion of one or both flanges of the bobbin that can be removed to expose the slice while the rest of the coil remains pinched between the intact portions of the flange structures. Of course, this step of exposing a portion of the coil (e.g., using break-away portions) is not necessary if a bobbin assembly having permanent slots is being employed, as shown in FIGS. 5C and 5D, for instance.

A lacing may be used to form bundles of adjacent turns of the coil so that the length and width of the bundles are of substantially the same dimension as the desired thickness of the coil (254). In one embodiment wherein the bundles have a circular cross-section, the diameter of the bundles is selected to be approximately the same dimension as the desired coil thickness. This step may be performed after all of the turns of the conductor are wound around the bobbin assembly, if desired.

In an alternative embodiment, rather than performing step 254 after all of the turns of the conductor are wound around the bobbin, steps 250 and 254 may be performed iteratively. In such an example, a predetermined number of conductor turns may be wound in step 250, followed by bundling that predetermined number with lacings in step 254. Another predetermined number of conductor turns may be wound around the bobbin, followed again by bundling this new set of windings, and so on. These two steps may be repeated for each bundle to be included in the coil structure, as described above in reference to FIGS. 5C and 5D. In such an embodiment, it may be desirable to utilize a bobbin structure having permanent slots, in which case step 252 may be omitted entirely.

In one embodiment, after all turns of the coil are wound, the inductance of the coil may be tested to determine whether it is within some tolerance of a predetermined inductance. In one case, the predetermined inductance is 1.22 millihenries. If it is not within some tolerance of the predetermined inductance, the total length of the conductor used to form the coil may be adjusted, either by removing a portion of the total length or adding to this total length. This may involve, for instance, removing a portion of a coil turn or adding a partial coil turn.

Regardless of the embodiment used to form the coil, the coil may next be positioned within a first-shot mold such that the top surface of the coil is substantially a same distance from the top surface of the mold as the bottom surface of the coil is from the bottom surface of the mold (255). The coil may be retained in this position by structures that extend around, and "pinch" the coil to hold it securely enough so the coil will not be displaced during the pressure exerted by the injection molding process. The structures are positioned around the coil at locations other than those that will receive the molding during the first-shot of injection process.

A first-shot of material may then be applied to create retention members at various locations around the coil (256). This first shot of material may be applied during an injection molding process that uses a polymer having characteristics described herein. In one particular embodiment, this is a CoolPoly™ thermoplastic elastomer exhibiting a high thermal conductivity. The retention members created during this first-shot are adapted to retain the coil at a centered position relative to the major surfaces of a second-shot mold that is used during a second-shot molding process.

A circuit assembly and optional stiffening member may be affixed to the coil (258). The coil assembly, including the coil and circuit assembly, is then placed in a second-shot mold such that the retention members position the coil so that it will reside substantially equidistant between the two major faces of the antenna (260). A second-shot of material is applied over the first-shot molding to create a coil configuration that is bi-directional, with the coil being substantially equidistant from the two major surfaces, or faces, of the antenna assembly (262).

One skilled in the art will appreciate that the molding process used to form antenna 78 may be performed in other ways. Many different types of molds may be used, and the process need not be limited to a two-step molding process.

Figure 10B:
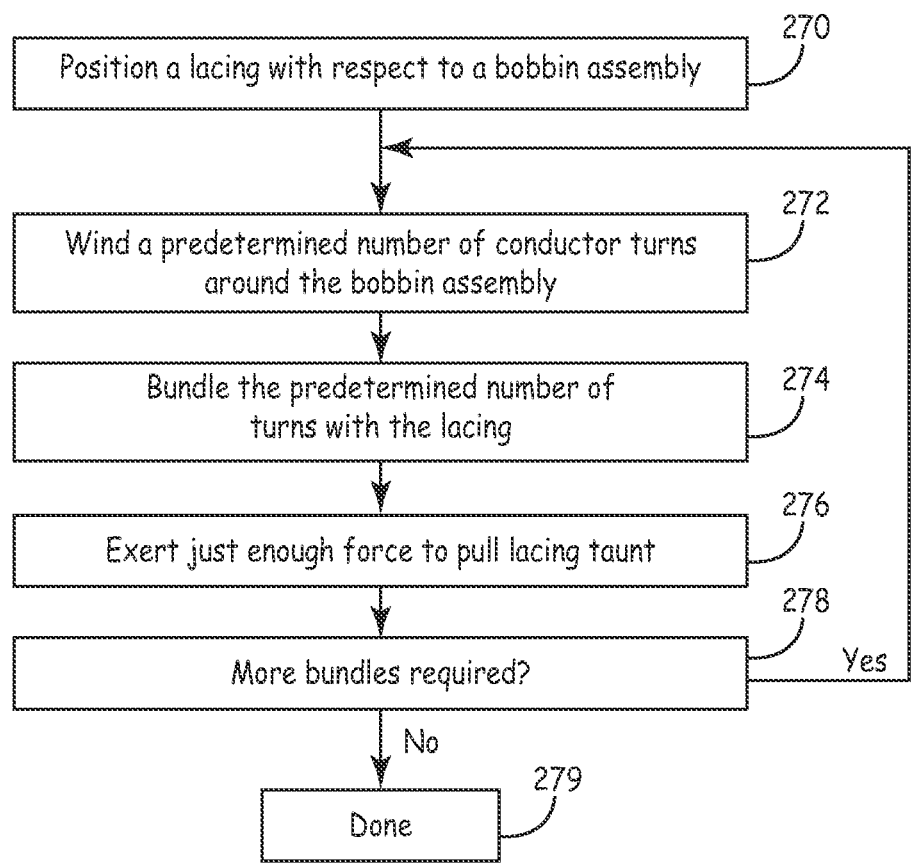
FIG. 10B is one example process of winding a conductor to form a coil according to aspects described herein.

FIG. 10B is one example process of winding a conductor to form a coil according to aspects described herein. In this example, lacing is applied during the winding process rather than after all turns of the conductor are wound onto a bobbin assembly in accordance with the example described above wherein steps 250 and 254 are iteratively performed. First, a lacing may be positioned to receive windings of a coil (270). In one example, this involves threading a lacing 155 through a pair of slots 141 of a bobbin assembly, as shown in FIG. 5D. In one example in which lacing carries an adhesive, the adhesive may be used to releasable hold the lacing in place substantially along one or more rods of the bobbin assembly.

Next, a predetermined number of turns of a conductor may be wound around the bobbin assembly (272). During this process, adhesive of the lacing (adhesive on single- or double-sided tape) may allow the lacing to remain substantially affixed to rods or other structures of the bobbin assembly so that the lacing is out of the way of the conductor being wound around the bobbin assembly.

The lacing may then be used to bundle the predetermined number of turns (274). This may be accomplished in any number of ways, including drawing the lacing through the slot so that opposite sides of the lacing "crisscross", by knotting the lacing, by twisting the lacing in 180 degree turns, and so on. In one example, during this process, the lacing is drawn just tight enough to remove any slack in the ends of the lacing so that the lacing is taunt, with no additional force being exerted beyond this to stretch the lacing, compress the bundles, or otherwise pack the adjacent turns of a bundle together (276). If more bundles are required (278), processing returns to step 270. Otherwise, the process is considered completed (279).

Figure 11:
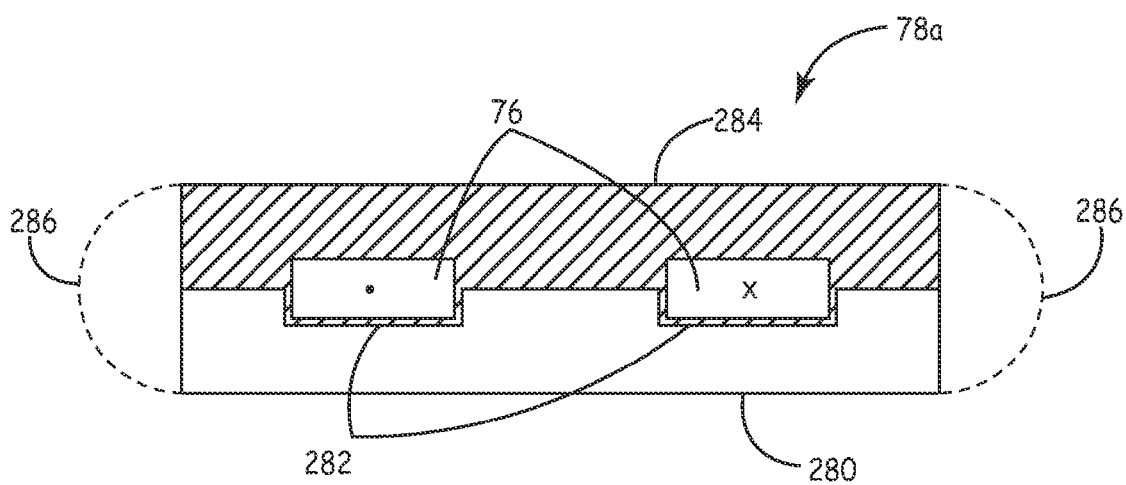
FIG. 11 is a conceptual diagram illustrating a cross-section of another embodiment of an antenna created using an alternative molding process.

FIG. 11 is a conceptual diagram illustrating a cross-section of an antenna 78a created using an alternative molding process. During a first step, a first-shot of material is applied to a mold that shapes a bottom portion 280 of antenna 78a. The mold includes a depression 282 that is substantially the same shape and size required to receive half the thickness of coil 76. Coil 76 (shown in cross-section in FIG. 11) is seated within depression 282 so that roughly half of the thickness of the coil remains outside of the bottom portion 280. Bottom portion 280 and coil 76 are then positioned within a second mold. A second-shot of material is applied to the second mold, forming a top portion 284 (shown hashed) of antenna 78. Because the second-shot of material will adhere to the bottom half 280 during application of that second shot, an integral structure is formed that encircles coil 76. Therefore, no additional steps are needed if desired. However, a third shot of material may be applied to provide added strength to the structure. In this case, the existing structure, including the top portion 284 and bottom portion 280 may be positioned within a third mold and a third shot of material may be applied to form a curved edge structure 286 (shown dashed). This edge 286 gives further support to the structure, holding portions 280 and 284 in position with respect to one another.

As is the case with antenna 78 described above, the resulting antenna 78a is bi-directional. That is, a top surface of coil 76 is roughly the same distance from a top surface of the antenna 78a as a bottom surface of coil is from a bottom surface of antenna 78a. As a result, the antenna will exhibit substantially the same operating characteristics, including coupling efficiency, regardless of which of the major surfaces is positioned closest to the patient. In other words, when antenna 78 is positioned in proximity to the patient for recharge and primary coil 76 is being driven with a predetermined signal, the amount of magnetic flux that will couple the primary coil 76 to the secondary coil will be substantially the same regardless of which of the major surfaces of the antenna is positioned against the patient.

Many other molding processes may be used to form antenna 78. In one case, the process may be a transfer molding operation rather than an injection molding process. As is known in the art, a transfer molding operation can be carried out at lower pressures. However, such a process may be more difficult to complete when using thermo plastic elastomer materials that become workable at higher temperatures.

Figure 12A:
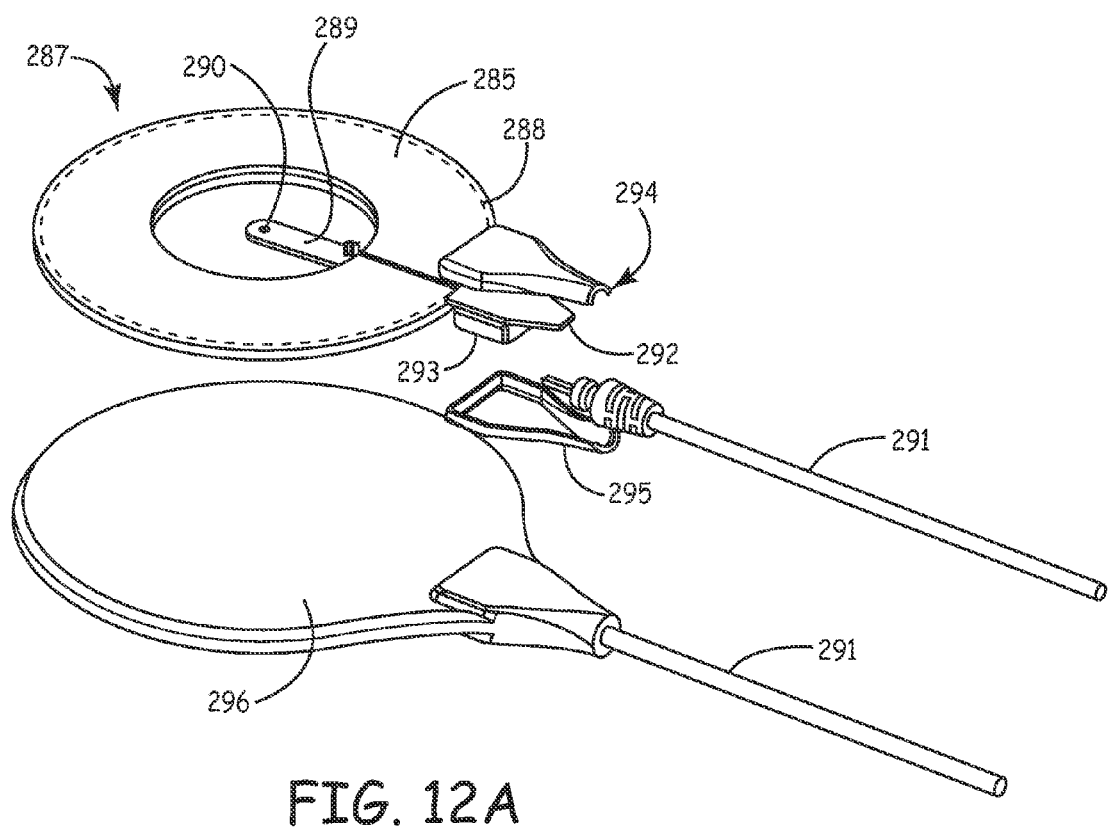
FIGS. 12A and 12B are a diagram of another embodiment of an antenna according to the current disclosure.
Figure 12B:
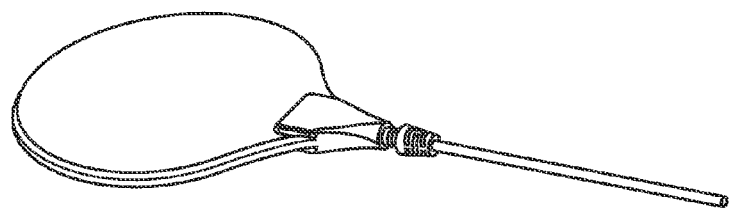

FIGS. 12A and 12B are diagrams of another embodiment of an antenna structure that may be formed according to the current disclosure. Coil assembly 287 includes coil 288 (shown dashed) and a first shot 285 of overmolding material that is applied over the coil. A stiffening member 289 carrying at least one temperature sensor 290 extends to a central location relative to coil 288 (e.g., a location that corresponds substantially with a position of a central axis of coil 288). Another temperature sensor (not shown) may be carried on the opposite side of stiffening member 289 at a similar location to provide temperature sensing capabilities that are optimized for either major surface of the antenna structure. In a manner similar to that described above, the stiffening member may be coupled to electrical conductors of cable 291 via conductive traces carried by flex circuit 292, a portion of which extends under the first shot 285 of overmolding material.

A tuning capacitor 293 may be electrically coupled to flex circuit 292 in a manner similar to that described above. The flex circuit 292 and tuning capacitor 293 may be housed within a protective case comprising first and second sides 294, 295 which may be held together using adhesive, opposing mating structures, or any other mechanism for affixing the two components one to another. The resulting housing protects the capacitor and conductive traces and provides strain relief for cable 291.

A second shot of material 296 may be applied to completely encase the first shot 285, stiffening member 289, temperature sensor 290, and, if desired, first and second sides 294, 295 of housing. The resulting antenna structure shown in FIG. 12B is a solid disk rather than a toroid such as shown in figures discussed above. If desired, the structure may be oblong rather than circular, or could take other shapes. As discussed above, in this embodiment, one or more temperature sensors are located at a point that would correspond substantially to the central axis of coil 288 rather than being at a location that is proximate to the windings of the coil.

According to another aspect, a holster may be provided to hold any of the antenna structures discussed above in a desired position with respect to a patient while the patient is using the antenna to recharge a rechargeable power source.

Figure 13:
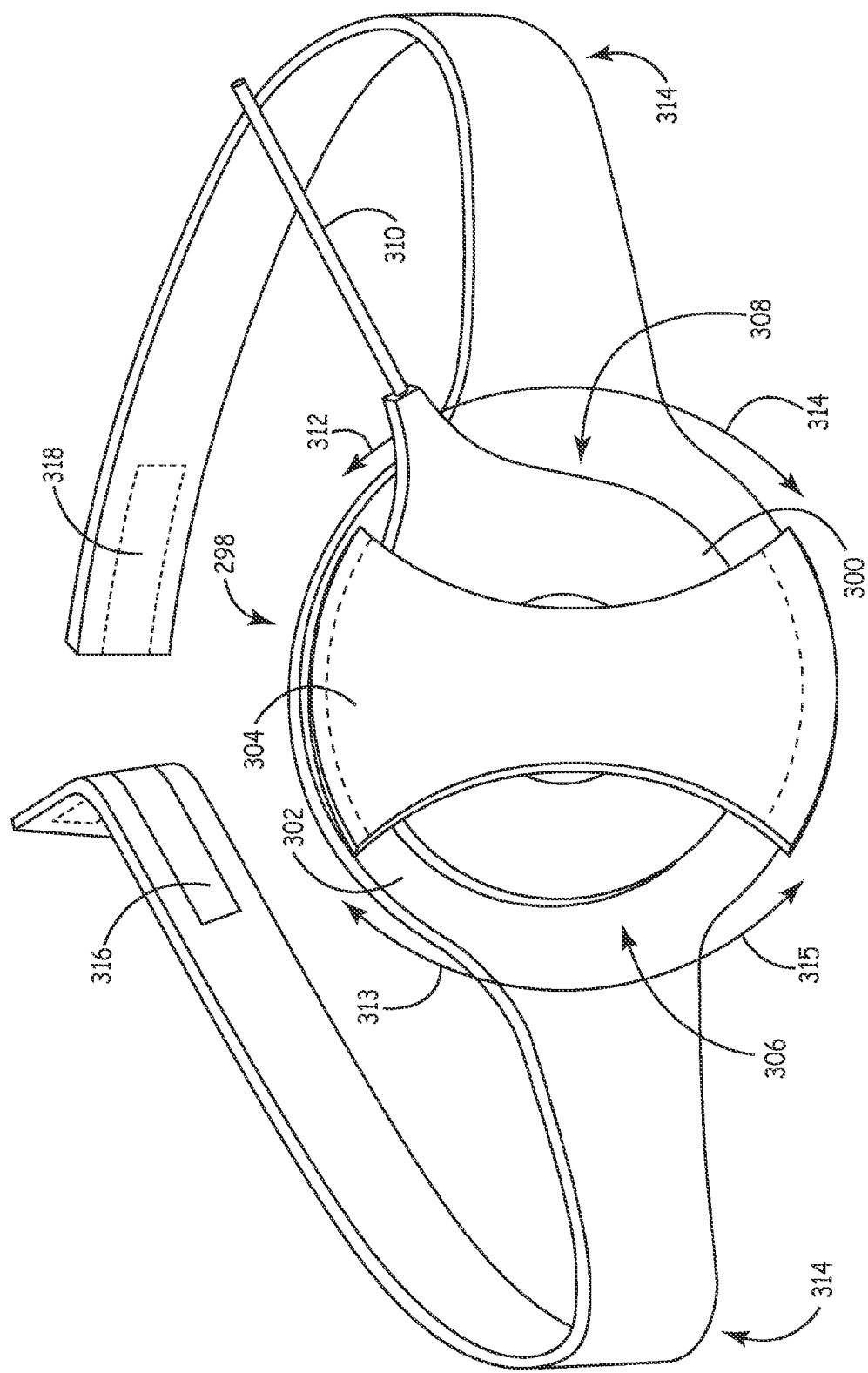
FIG. 13 is a perspective view of one embodiment of a holster that may be used to carry an antenna according to any of the embodiments described herein.

FIG. 13 is a perspective view of one embodiment of a holster 298 that may be used to carry an antenna 300, which may be an antenna formed in any of the ways described above. Holster includes a base portion 302 and a retaining member 304 coupled to the base portion to form a pocket that is sized to retain antenna 300. Retaining member 304 may be retained in relation to base portion 302 using stitching, adhesives, zippers, opposing hook-and-loop fasteners such as Velcro® fasteners, buttons, snaps, clips, clasps, or any other desired retention mechanism(s).

As discussed above, base portion 302 and retaining member 304 form a pocket sized to receive antenna 300. In one embodiment, antenna 300 may be inserted into pocket from either a first side 306 or a second side 308 such that a cable 310 of antenna 300 is located on a desired side of the patient's body. Moreover, the antenna is rotatable within the pocket so that cable 310 of antenna may be positioned in an upwards orientation, as indicated by arrows 312 and 313, in a downwards position, as indicated by arrows 314 or 315, or at any point there between. In one embodiment, antenna 300 may be rotated by at least 90 degrees when inserted into the pocket from either side. In a more particular embodiment, the antenna may be rotated between 90 and 120 degrees when inserted within the pocket from either the first side 306 or the second side 308. The pocket is sized so that antenna 300 fits loosely enough that it can be readily rotated so that the cable 310 is in a desired location, but snugly enough to maintain that desired position once that orientation has been selected. Holster 298 thereby allows a user to position cable 310 in any desired position that is comfortable for the patient.

Holster 298 may include straps 314 that may be integrated with base portion 302 or may otherwise be coupled to base portion 302 (e.g., via stitching, adhesive, zippers, opposing hook-and-loop fasteners such as Velcro® fasteners, buttons, snaps, clips, clasps, or any other desired retention mechanism.) The straps may be designed to encircle a portion of the patient's body, which will generally be a portion of the patient's torso (e.g., chest, waist etc.) However, in another embodiment, the straps may be adapted to encircle another portion of the patient's body, including a leg, arm, head, and so on.

The opposing sides of straps 314 may include fastening members to allow them to be coupled one with another. For instance, one side of a first strap 314 may include a portion 316 carrying hook members while an opposing portion 318 on the other side of the other strap may carry loop members to provide hook-and-loop fastening capability such as is provided by Velcro® fasteners. In another embodiment, buttons, snaps, mechanical-type hooks, clips, a releasable reusable adhesive, clasps, ties, a zipper, or any other type of fastening member(s) may be used to fasten one strap to another. In yet another scenario, the two ends of the straps 314 may simply be tied together.

Base portion 302 in one embodiment may include a cut-away portion (not shown) that allows at least a portion of a surface of antenna 300 to directly contact a surface of a patient (or the patient's clothing). This may enhance the coupling efficiency between the primary and secondary coils.

Base portion 302, retaining member 304 and strap 314 may be formed of a material that can be comfortably worn against the skin of the patient. Such a fabric may include a breathable fabric that wicks away moisture, such as is produced by Under Armour. Alternatively or additionally, nylon, cotton, polyester, leather, or some other durable, moisture-resistant material may be used in one or more of these structures. Any one or more of base portion 302, retaining member 304, and strap 314 may additionally or alternatively be fashioned of cushioned, quilted, elastic, and/or foam materials which may be moisture-wicking to enhance patient comfort. In one embodiment, one or more of these structures may be formed of a memory foam that is adapted to provide a soft comfortable surface that adheres to and retains the shape of the patient's body.

In the embodiment shown in FIG. 13, holster 298 is bidirectional such that either of ties 314 may encircle a left or a right portion of a patient's body. Stated otherwise, there is no "top" or "bottom" of holster 298, which may be oriented in any position so long as base portion 302 is the surface positioned towards the patient's body with retaining member 304 positioned facing "outwards". This bidirectional aspect of the holster makes it easy for the patient to use. Moreover, because antenna 300 may be inserted from either side 306 or 308 of the pocket, the patient may easily position the antenna in the pocket so that cable 310 is on a desired side of the patient's body. Finally, during this process of positioning antenna 300 within the pocket, the patient need not be concerned about which major surface of the antenna 300 is positioned towards his/her body, since in one embodiment, the antenna is bi-directional and will perform substantially the same regardless of orientation. Thus, the holster and antenna may both be bidirectional, making them easy to don and operate, with little thought required on the part of the patient as to the appropriate orientation of, or interrelationship between, the various components of the system.

Various techniques and embodiments are described herein. For instance one technique involves lacing turns of a coil to obtain a flexible coil structure. Other techniques are described for forming a bi-directional antenna structure from the resulting coil. Still other aspects are described. It will be appreciated that the various aspects may be practiced alone or in conjunction with one another. For instance, the lacing process discussed above may be employed to provide a flexible coil. Thereafter, this flexible coil may then be included in an antenna that need not be bi-directional (that is, opposite major surfaces of the coil can be, but need not be, substantially equidistant from a corresponding surface of antenna.) As another example, any resulting embodiment of the antenna may be employed with, or without, the bi-directional holster of FIG. 13. Thus, various techniques described herein may be practiced in any combination. The specific embodiments described are to be considered exemplary only and not limiting and the present disclosure is limited only by the claims that follow.

What is claimed is:

1. A charging system adapted to charge a power source of an implantable medical device, comprising:
   a coil having multiple turns and being adapted to transcutaneously transfer an electromagnetic waveform to the implantable medical device;
   lacing adapted to group the turns of the coil into multiple bundles, each containing a predetermined number of adjacent ones of the turns; and
   a flexible overmolding formed over the coil; and
   wherein each of the multiple bundles of the coil contains fewer than all of the multiple turns of the coil.

2. The system of claim 1, wherein the lacing comprises a flexible tape having adhesive adapted to adhere to the turns of the coil.

3. The system of claim 2, wherein the lacing is woven between adjacent ones of the bundles.

4. The system of claim 1, further comprising multiple sets of lacing, each set being woven between adjacent ones of the bundles.

5. The system of claim 4, further comprising at least four sets of lacing.

6. The system of claim 1, wherein the predetermined number of adjacent turns is selected so each bundle has a length and width that is of substantially a same dimension as a thickness of the coil.

7. The system of claim 6, wherein the predetermined thickness of the coil is no greater than .165 inches.

8. The system of claim 1, wherein the flexible overmolding is formed of a thermoplastic elastomer.

9. The system of claim 1, further comprising:
   an external device adapted to exchange data with the implantable medical device; and
   a cable adapted to detachably couple the coil to the external device.

10. The system of claim 1, wherein the overmolding forms a structure having two major surfaces, and wherein the coil is substantially centered between the surfaces.

11. The system of claim 1, further comprising a tuning capacitor that is positioned in proximity to the coil.

12. The system of claim 1, further comprising:
   a cable adapted to couple the coil to a source of power; and
   a circuit carried by the cable that is adapted to generate a signal within the coil.

13. The system of claim 12, wherein the circuit is adapted to generate a signal to at least one of provide data or provide power transcutaneously to the implantable medical device.

14. The system of claim 12, wherein the circuit is configured based on a characteristic of the coil.

15. The system of claim 12, wherein the circuit is configured based on a characteristic of the IMD.

16. The system of claim 1, further comprising at least one temperature sensor adapted to provide an indication of temperature associated with operation of the coil.

17. The system of claim 1, further comprising an external device adapted to communicatively couple to the coil, the external device being further adapted to at least one of:
   exchange data with the implantable medical device,
   initiate the recharge of the power source of the implantable medical device,
   control the recharge of the power source of the implantable medical device, and
   provide status regarding the recharge of the power source of the implantable medical device.

18. The system of claim 17, wherein the external device is a portable handheld device.

19. The system of claim 1, and further comprising an implantable medical device comprising a power source adapted to be recharged via the coil.

20. A system to transcutaneously recharge a power source of an implantable medical device, comprising:
- a primary coil having multiple turns; and
- lacing adapted to group adjacent ones of the turns of the coil into bundles, each bundle having a dimension that is substantially the same as a dimension of the primary coil wherein the lacing is formed of multiple sets of lacing that are substantially equally spaced around a circumference of the primary coil.

21. The system of claim 20, wherein each bundle has a diameter that is substantially the same as a thickness of the primary coil.

22. The system of claim 20, wherein each bundle has a length and a width that are each substantially the same as a thickness of the primary coil.

23. The system of claim 20, further comprising:
- a circuit assembly adapted to drive the primary coil with at least one of a recharge signal and a communication signal; and
- a cable coupled to the primary coil that carries the circuit assembly.

24. The system of claim 20 wherein the implantable medical device comprises a secondary coil adapted to receive energy from the primary coil to transcutaneously recharge the power source, further comprising an overmolding applied to at least one surface of the primary coil to form an antenna having first and second major surfaces, and wherein coupling efficiency between the primary coil and the secondary coil is substantially the same regardless of which of the first and second major surfaces of the antenna is positioned closest to the secondary coil when the secondary coil is receiving energy from the primary coil.

25. The system of claim 24 further comprising first and second temperature sensors, each adapted to provide a temperature associated with a respective one of the first and second major surfaces when the secondary coil is receiving energy from the primary coil.

26. The system of claim 20, further comprising an implantable medical device comprising a power source and a secondary coil adapted to receive energy from the primary coil to transcutaneously recharge the power source of the implantable medical device.

27. The system of claim 20, further comprising an external device adapted to communicatively couple to the primary coil, the external device being further adapted to at least one of:
- exchange data with the implantable medical device,
- initiate the recharge of the power source of the implantable medical device,
- control the recharge of the power source of the implantable medical device, and
- provide status regarding the recharge of the power source of the implantable medical device.

28. A system to transcutaneously recharge a power source of an implantable medical device, comprising:
- a primary coil having multiple turns;
- lacing adapted to group adjacent ones of the turns of the coil into bundles, each bundle having a dimension that is substantially the same as a dimension of the primary coil; and
- a holster having a pocket with a first side and a second side, the pocket adapted to receive the primary coil from either the first side or the second side.

29. The system of claim 28, wherein the primary coil may be rotated by at least 90 degrees within the pocket when received from either the first side or the second side of the pocket.

30. A method of making an antenna, comprising:
- winding a conductor to form a coil having multiple turns and first and second surfaces;
- grouping adjacent turns of the coil into bundles, each having a dimension that is substantially the same as a predetermined thickness of the coil; and
- providing a flexible insulation over the coil, wherein each of the bundles includes a predetermined number of the turns, wherein winding the conductor comprises winding the predetermined number of turns around a rod, wherein grouping the adjacent turns comprises grouping the predetermined number of turns into a bundle, and further comprising repeating the winding and the grouping steps for each of the bundles to be included in the coil.

31. The method of claim 30, wherein each bundle has a length that is the same as the predetermined thickness of the coil.

32. The method of claim 30, wherein providing the flexible insulation comprises:
- providing a first shot of material to form retaining members over the coil;
- positioning the retaining members within a second shot mold; and
- providing a second shot of material so that a first major surface of the antenna is substantially a same distance from the first surface of the coil as a second major surface of the antenna is from the second surface of the coil.

33. The method of claim 30, comprising:
- providing a cable carrying a circuit assembly; and
- coupling the cable to the coil to allow a circuit of the circuit assembly to drive the coil.

34. A system, comprising:
- a coil having multiple turns and being adapted to transcutaneously transfer an electromagnetic waveform to an implantable medical device;
- lacing adapted to group the turns of the coil into multiple bundles, each containing fewer than all of the multiple turns of the coil;
- a flexible overmolding formed over the coil; and
- an external device adapted to communicatively couple to the coil and to the implantable medical device.

35. The system of claim 34, further comprising an implantable medical device adapted to receive the electromagnetic waveform from the coil having multiple turns.

36. The system of claim 35, wherein each bundle has a dimension that is substantially the same as a dimension of the coil.

* * * * *